(12) United States Patent
Albert et al.

(10) Patent No.: US 8,481,758 B2
(45) Date of Patent: Jul. 9, 2013

(54) PROCESS FOR THE PRODUCTION OF PROSTAGLANDINS AND PROSTAGLANDIN ANALOGS

(75) Inventors: Martin Albert, Bruck am Ziller (AT); Andreas Berger, Ebbs (AT); Dominic De Souza, Regau (AT); Kerstin Knepper, Woergl (AT); Hubert Sturm, Innsbruck (AT)

(73) Assignee: Sandoz AG, Basel (CH)

( * ) Notice: Subject to any disclaimer, the term of this patent is extended or adjusted under 35 U.S.C. 154(b) by 135 days.

(21) Appl. No.: 12/500,669

(22) Filed: Jul. 10, 2009

(65) Prior Publication Data

US 2010/0010239 A1    Jan. 14, 2010

Related U.S. Application Data

(60) Provisional application No. 61/079,624, filed on Jul. 10, 2008.

(30) Foreign Application Priority Data

Jul. 10, 2008   (EP) ..................................... 08160099

(51) Int. Cl.
*C07D 307/93*    (2006.01)
*C07C 69/76*    (2006.01)

(52) U.S. Cl.
USPC ............................................. 549/302; 560/60

(58) Field of Classification Search
USPC ............................................. 549/302; 560/60
See application file for complete search history.

(56) References Cited

U.S. PATENT DOCUMENTS 3,985,791 A * 10/1976 Muchowski et al. ............ 560/55
5,359,095 A * 10/1994 Resul ............................. 549/305
6,689,901 B2 * 2/2004 Henegar ......................... 562/465

OTHER PUBLICATIONS

Cadierno et. al. Chem. Commun., 2007, 2536-2538.*

* cited by examiner

*Primary Examiner* — Nizal Chandrakumar
(74) *Attorney, Agent, or Firm* — Luedeka Neely Group, P.C.

(57) ABSTRACT

The present invention relates to an improved process for the production of prostaglandins and prostaglandin analogs. In particular, this invention relates to the production of prostaglandins of the $PGF_{2\alpha}$-series, including latanoprost, travoprost, and bimatoprost, which are active pharmaceutical ingredients used for the reduction of elevated intra-ocular pressure in patients with glaucoma and ocular hypertension.

13 Claims, No Drawings

PROCESS FOR THE PRODUCTION OF PROSTAGLANDINS AND PROSTAGLANDIN ANALOGS

CLAIM OF PRIORITY TO PRIOR FILED APPLICATIONS

This application claims priority to U.S. Provisional Application Ser. No. 61/079,624 entitled "Process for the Production of Prostaglandins and Prostaglandin Analogs" filed on Jul. 10, 2008, the content of which is incorporated herein by reference in its entirety. This application also claims priority to European Patent Application Serial Number 08160099.1 filed on Jul. 10, 2008, the content of which is incorporated herein by reference in its entirety.

FIELD OF THE INVENTION

The present invention relates to an improved process for the production of prostaglandins and prostaglandin analogs. In particular, this invention relates to the production of prostaglandins of the $PGF_{2\alpha}$-series, including latanoprost, travoprost, and bimatoprost, which are active pharmaceutical ingredients used for the reduction of elevated intra-ocular pressure in patients with glaucoma and ocular hypertension.

BACKGROUND OF THE INVENTION

Prostaglandins are a family of biologically active compounds that are found in virtually all tissues and organs. These naturally occurring prostaglandis have extremely complex biological functions (e.g. stimulation of smooth muscles, dilation of smaller arteries and bronchi, lowering blood pressure, etc.). Synthetic prostaglandins are for example clinically used to induce childbirth or abortion, to prevent and treat peptic ulcers, to treat pulmonary hypertension, or in treatment of glaucoma and ocular hypertension.

Prostaglandin $F_{2\alpha}$ ($PGF_{2\alpha}$-(Z)-7-((1R,2R,3R,5S)-3,5-dihydroxy-2-((S,E)-3-hydroxyoct-1-enyl)cyclopentyl)hept-5-enoic acid)) has the structure:

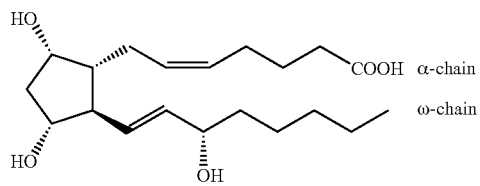 [SMILES: CCCCC[C@H](O)/C=C/[C@@H]1[C@@H](C/C=C\CCCC(=O)O)[C@@H](O)C[C@H]1O]

The $PGF_{2\alpha}$-derivatives are thus characterized by two hydroxyl groups in cis configuration relative to the cyclopentane ring, and two side chains in a trans configuration relative to each other. Analogs of $PGF_{2\alpha}$ may have a different number of double bonds in the side chains and the substituents along the side chains as well as the length of the side chains may vary. The Z-configured double bond in the α-chain is a common feature in pharmaceutically active $PGF_{2\alpha}$ analogs, whereas the double bond in the ω-chain may be missing (e.g. latanoprost and unoprostone). The carboxylic acid function may be esterified (in particular isopropyl esters proved to be clinically useful e.g. latanoprost and travoprost) or converted into an amide (e.g. bimatoprost).

Examples for $PGF_{2\alpha}$-derivatives having therapeutic use are latanoprost (general formula (A)), having a saturated ω-chain bearing a phenyl substituent and wherein the carboxylic acid in the α-chain is esterified, travoprost (general formula (B)), containing a trifluoromethylphenyl ether in the ω-chain and wherein the acid function in the α-chain is also esterified, and bimatoprost (general formula (C)), having a phenyl substituent in the ω-chain and wherein the acid function in the α-chain is converted into an amide.

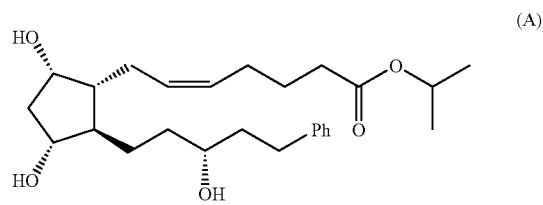

(A)

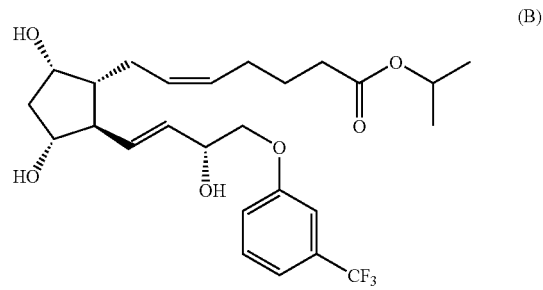

(B)

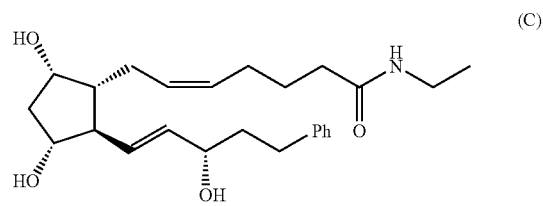

(C)

All three compounds shown above are used in the clinic to treat glaucoma and ocular hypertension.

$PGF_{2\alpha}$-analogs for use in treatment of glaucoma and ocular hypertension are described for example in EP 0 364 417 A1 (Pharmacia AB). In this patent a number of $PGF_{2\alpha}$-analogs with variations in the ω-chain are described. The synthesis disclosed follows to a large extent the original route of Corey et al. (Corey, E. J.; Weinshenker, N. M.; Schaaf, T. K.; Huber, W. J. Am. Chem. Soc. 1969, 91, 5675-5677; Corey, E. J.; Noyori, R.; Schaaf, T. K. J. Am. Chem. Soc. 1970, 92, 2586-2587.) and is shown in scheme 1 for the preparation of 17-phenyl-18,19,20-trinor-$PGF_{2\alpha}$-isopropy ester.

The starting material disclosed in EP 0 364 417 A1 is commercially available p-phenyl-benzoyl (PPB) protected Corey lactone 1, which is converted into the corresponding aldehyde 2 by oxidation using DCC/DMSO. Compound 2 is not isolated but reacted in solution with an appropriate phosphonium salt to give intermediate 3. Reduction of the ketone in compound 3 forms the corresponding alcohol 4 as a mixture of diastereomers. After deprotection to form diol 5 the lactone is selectively reduced to the lactol 6 which was purified using column chromatography. A subsequent Wittig reaction forms acid 7 which is converted into the desired product 8 by esterification using isopropyl iodide.

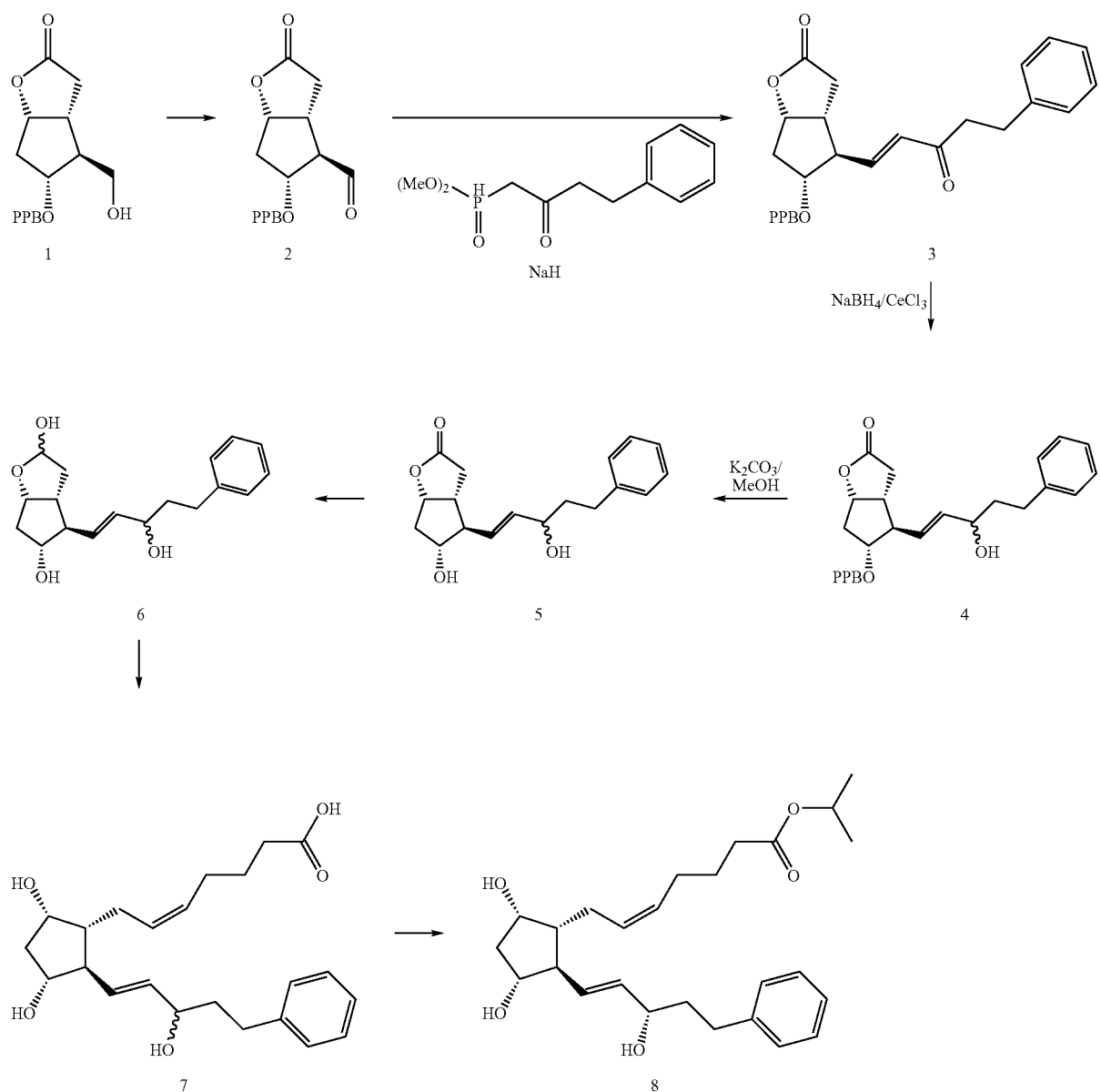

Scheme 1

For the synthesis of latanoprost the above shown synthetic route is only altered in that way, that the 13,14-double bond of enone 3 is reduced using 10% Pd/C under hydrogen atmosphere to give the corresponding ketone intermediate with a saturated ω-side chain. The next steps (reduction of the ketone, deprotection, reduction of the lactone, Wittig reaction and esterification) are performed as described above to give latanoprost which was purified using preparative liquid chromatography.

An improved synthesis for such 13,14-dihydro $PGF_{2\alpha}$-analogs is described in U.S. Pat. No. 5,359,095 (Pharmacia AB). Again, as shown in scheme 2 for the preparation of latanoprost, the disclosed starting material is the PPB-protected Corey lactone 1 which is converted in similar way to the enone 3 as described above. As the original reduction of the ketone only gave 37% yield of the desired 15S-alcohol 9, L-selectride was used as reducing agent, improving the diastereoselectivity of the reduction and increasing the yield of 9 to 60%. It had been found that the allylic alcohol in compound 9 is deoxygenated on hydrogenation of the double bond over palladium catalyst. Therefore, protection of the allylic alcohol seemed to be necessary. This was accomplished by deprotection of compound 9 to afford diol 10 followed by protection of both hydroxyl groups with THP to give compound 11. Reduction of the 13,14-double bond in compound 11 using Pd/C in an hydrogen atmosphere gave compound 12 in almost quantitative yield. Reduction of the lactone moiety in compound 12 afforded lactol 13 in 76% yield. Consecutive Wittig reaction and esterification gave compound 15 in 57% yield after flash chromatography as an oil. Acidic deprotection of the THP groups afforded desired latanoprost in 78% yield. However, this sequence involves two additional steps (protection/deprotection).

Scheme 2

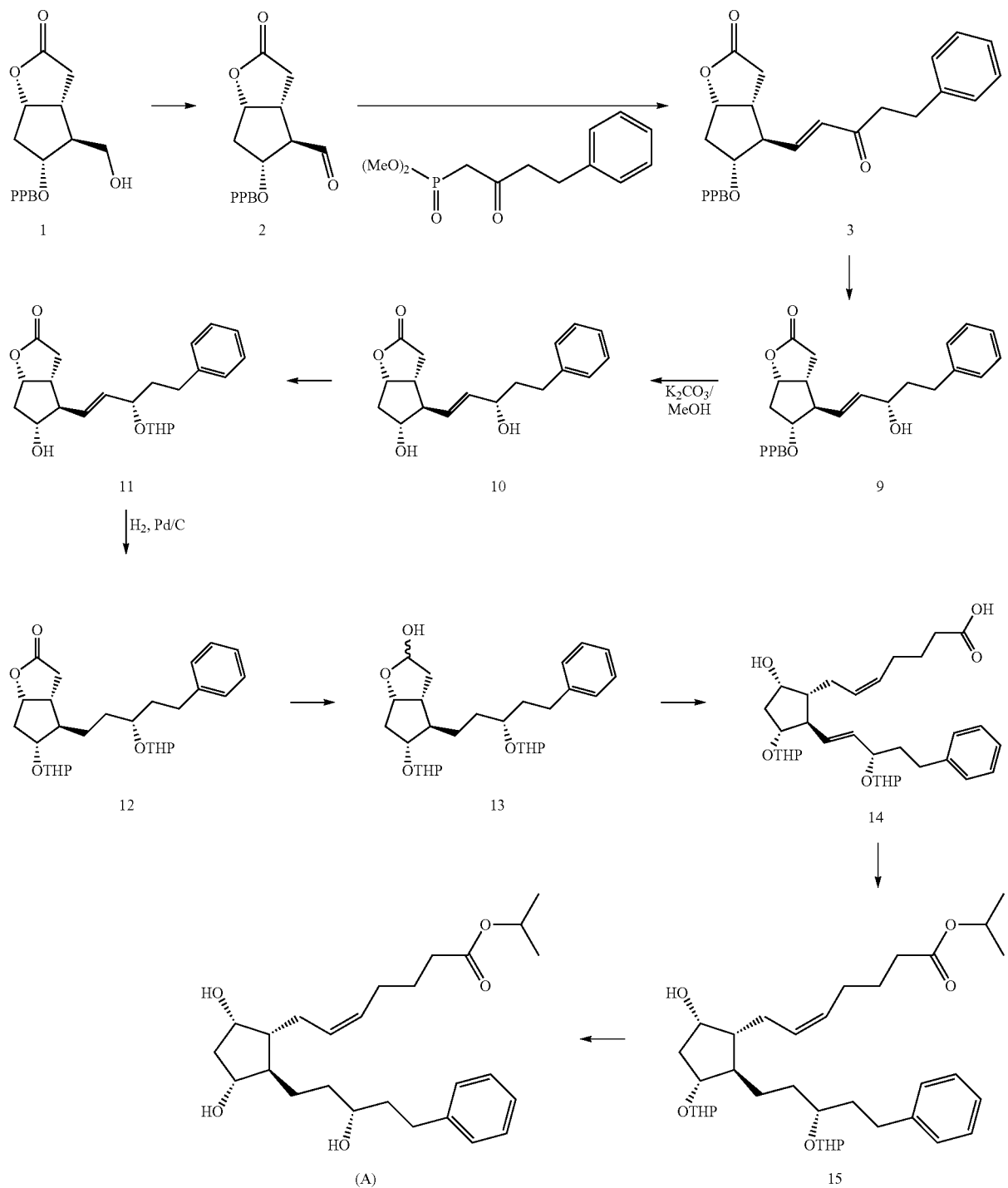

In WO 2001/55101 (Finetech) another process for the synthesis of latanoprost is disclosed. In this International patent application a more effective stereoselective reduction of enone 3 is described using (−)-B-chlorodiisopinocamphenylborane [(−)-DIP-Cl] or borane in the presence of CBS-oxazaborolydines to give the desired 15S-alcohol 9 with a diastereomeric excess (de) of 92%. The reduction of the corresponding benzoyl-protected enone using (−)-DIP-Cl has been described previously in U.S. Pat. No. 5,698,733 (Alcon) giving a similar diastereomeric excess.

The free alcohol is protected using the THP group and purified by crystallization. At this stage the unwanted 15R-isomer in the mother liquor may be recycled to 3 using a deprotection-oxidation sequence. The remaining steps to the desired latanoprost are performed similar to the processes described above with modifications concerning the protecting group strategy.

International patent application WO 2006/094294 (Teva) describes another methodology to deplete unwanted 15R-isomer using enzymatic acylation or enzymatic ester hydrolysis.

Patent applications WO 2002/096898 (Resolution Chemicals) and US 2007/0167641 (Chirogate) describe the use of silyl protecting groups in the preparation of $PGF_{2\alpha}$-analogs.

In the European patent application EP 1721894 A1 (Technopharma) an alternative method for the reduction of the lactone to the lactol using a silane in the presence of a titanocene is described.

The processes described in the state of the art have the drawback that the reduction of the 13-14-double bond is performed using catalytic hydrogenation. This methodology involves the use of hazardous hydrogen gas. The processes disclosed require elaborate protecting group strategies. Furthermore, the isolation of many intermediates is necessary and the process is laborious and less efficient.

OBJECTS OF THE INVENTION

It is an object of the invention to provide a novel and improved process for the preparation of prostaglandins or prostaglandin analogs in good yields, in large amounts and with desired purity.

It is also an object of the invention to provide a process for the preparation of prostaglandins or prostaglandin analogs that involves a minimum amount of isolated intermediates and therefore simplifies the process.

A further aspect of the invention is to provide a method to obtain high purity prostaglandins or prostaglandin analogs.

SUMMARY OF THE INVENTION

The above objects are achieved by the present invention, which provides a process for the preparation of prostaglandins or prostaglandin analogs, in particular prostaglandins of the formula 16,

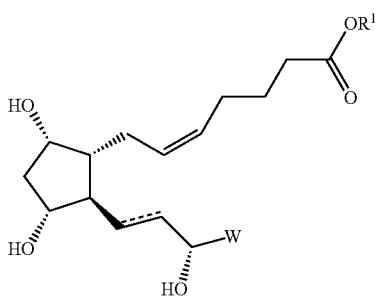

16 wherein $R^1$ is selected from $C_1$-$C_6$ alkyl; W is selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$; and ----- represents a double bond or a single bond.

The present invention relates to a process for preparing a prostaglandin or prostaglandin analog at least comprising step (i):

(i) reduction of a compound of general formula (I)

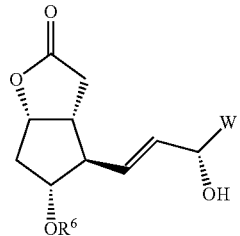

(I)

under transfer hydrogenation conditions to obtain a compound of general formula (II)

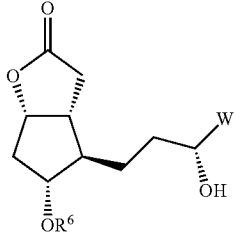

(II)

wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents H or $R^2$ with $R^2$ being a hydroxyl protecting group.

DETAILED DESCRIPTION OF THE INVENTION

The present invention relates to a process for preparing a prostaglandin or prostaglandin analog at least comprising step (i):

(i) reduction of a compound of general formula (I)

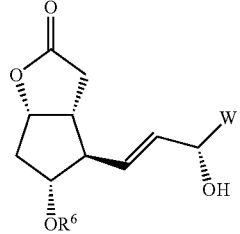

(I)

under transfer hydrogenation conditions to obtain a compound of general formula (II)

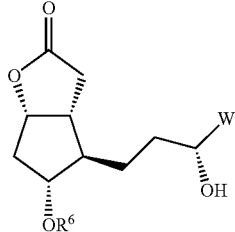

(II)

wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents H or $R^2$ with $R^2$ being a hydroxyl protecting group.

Preferably, the prostaglandin or prostaglandin analog is a prostaglandin of general formula 16:

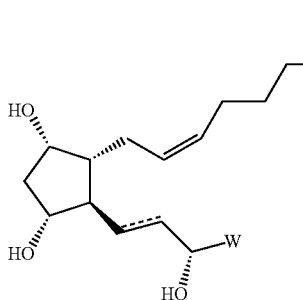

16 wherein $R^1$ is selected from $C_1$-$C_6$ alkyl

╌╌╌ represents a double bond or a single bond, and

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$.

The process according to the present invention is particularly suitable for preparing latanoprost and travoprost.

According to one embodiment, the present invention therefore relates to a process for preparing a prostaglandin or prostaglandin analog as disclosed above, wherein the prostaglandin is a prostaglandin of general formula 16:

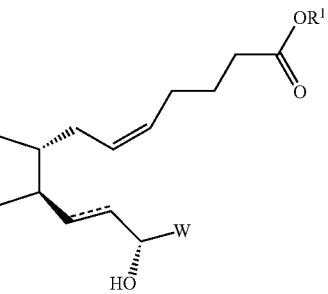

16 wherein $R^1$ is selected from $C_1$-$C_6$ alkyl

╌╌╌ represents a double bond or a single bond, and

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$.

The process according to the present invention comprises at least step (i):

(i) reduction of a compound of general formula (I)

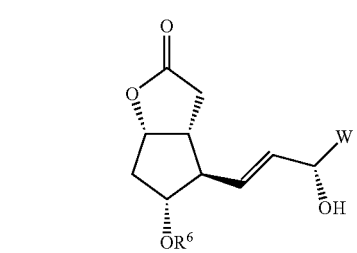

(I)

under transfer hydrogenation conditions to obtain a compound of general formula (II)

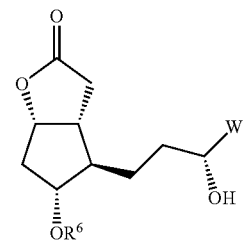

(II)

wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents H or $R^2$ with $R^2$ being a hydroxyl protecting group.

The process of the present invention allows the reduction of the 13-14 double bond in compounds of formula (I) without the use of hydrogen gas, omitting the safety measurement associated with it.

Depending on the over-all process, the hydrogenation can take place at different stages of the preparation process.

The compound of general formula (I) can have a protected or unprotected hydroxyl group. In a process for preparing a prostaglandin or prostaglandin analog according to the present invention, step (i) can be carried out before or after an deprotection step.

In case residue $R^6$ represents a hydrogen, step (i) is generally carried out after a deprotection step.

In case residue $R^6$ represents a hydrogen, the compound of general formula (I) represents a compound of formula 22. In particular for the synthesis of latanoprost, compounds of formula 22 are hydrogenated under transfer hydrogenation conditions, to give compounds of formula 23,

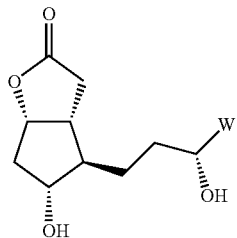

23 wherein W is defined as above.

In case residue $R^6$ represents a residue $R^2$, step (i) is generally carried out before a deprotection step.

In case residue $R^6$ represents a residue $R^2$, the compound of general formula (I) represents a compound of formula 21. Thus, compounds of formula 21 are hydrogenated under transfer hydrogenation conditions, to give compounds of formula 27,

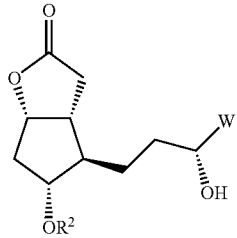

27 wherein W and $R^2$ are defined as above, which might be deprotected according to the present invention to give compounds of formula 23.

According to the present invention, the hydrogenation according to step (i) is a hydrogenation under transfer hydrogenation conditions. Said transfer hydrogenation conditions comprise the use of a suitable hydrogen-donor in the presence of a suitable catalyst. Suitable hydrogen-donors include carboxylic acids and carboxylic acid derivatives such as formic acid and the salts and derivatives thereof, alcohols such as isopropanol, readily dehydrogenatable hydrocarbons such as cyclohexadiens, hydrazine, silanes, amines, and mixtures thereof. It is preferred to use formic acid and the salts thereof. Suitable catalyst include Raney nickel and noble metal catalysts such as rhodium, palladium, and platinum. Preferred noble metal catalysts are based on palladium and platinum. It is preferred to use the catalyst in an amount of about 0.1% to about 50% relative to the amount of compounds of the formula (I), in particular of formula 21 or 22, more preferably 1%-25% of catalyst is used. It is preferred to run the reaction in an organic solvent. Compounds of the formula (II), in particular of formula 27 or 23 can be isolated and purified by methods know to a person skilled in the art but it is preferred not to isolate compounds of formula (II), in particular of formula 27 or 23 but use them in solution as obtained after work-up for the next step.

According to a preferred embodiment, the present invention is therefore directed to a process for preparing a prostaglandin or prostaglandin analog as disclosed above, wherein the reduction under transfer hydrogenation conditions according to step (i) comprises the use of a hydrogen-donor selected from carboxylic acids and carboxylic acid derivatives such as formic acid and the salts and derivatives thereof, alcohols such as isopropanol, readily dehydrogenatable hydrocarbons such as cyclohexadiens, hydrazine, silanes, amines, and mixtures thereof in the presence of a catalyst selected from Raney nickel and noble metal catalysts such as rhodium, palladium, and platinum.

In step (i), a compound of general formula (I) is reacted.

The compound of the general formula (I) can be prepared according to any suitable method according to the present invention. Preferably, the compound of general formula (I) is prepared using a process with only few protection group modifications.

In case the residue $R^6$ in the formula (I) represents $R^2$, i.e. a hydroxyl protecting group, the compound of formula (I) is preferably obtained by a process comprising the steps (a) oxidation of a compound of general formula 17,

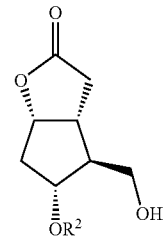

17 to obtain a compound of general formula 18,

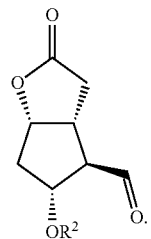

18

(b) Wittig reaction of the compound of formula 18 to obtain a compound of formula 20

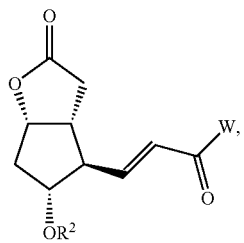

(c) reduction of the compound of formula 20 to obtain a compound of formula 21

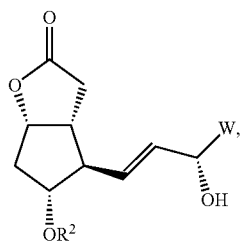

wherein W and $R^2$ are defined as disclosed above.

In case the residue $R^6$ represents hydrogen in formula (I), an additional deprotection step might be carried out.

According to step (a), a compound of general formula 17, is oxidised

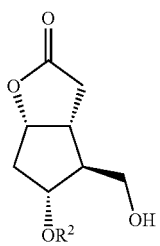

to obtain a compound of general formula 18

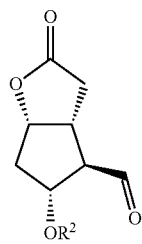

wherein $R^2$ represents a hydroxyl protecting group.

Suitable hydroxyl protecting groups are listed for example in T. W. Greene, "*Protective Groups in Organic Chemistry*", John Wiley & Sons, New York (1981). It is preferred to use esters of carboxylic acids as hydroxyl protecting groups. Most preferably, benzoyl- and substituted benzoyl esters are used.

Preferably the oxidation according to step (a) is a selective oxidation of a compound of the formula 17. The selective oxidation of compounds of the formula 17 to give compounds of the formula 18 is preferably carried out by employing commonly used oxidizing reagents such as activated dimethyl sulfoxide (DMSO) and related reagents (e.g. dimethylsulfide activated with N-chlorosuccinimide) as described in Tidwell *Synthesis* 1990, 857-870 and modifications thereof. The oxidation can also be carried out using Dess-Martin reagent, manganese-, chromium- or selenium reagents, tertiary amine oxides or via radical oxidation procedures using for example catalytic amounts of TEMPO in combination with inexpensive co-oxidants such as NaOCl.

Preferably DMSO is used in combination with a number of activating agents comprising oxalyl chloride, $SO_3$.pyridine, DCC, EDC.HCl, trifluoroacetic anhydride. Most preferably, DMSO in combination with oxalyl chloride is used. Such DMSO mediated oxidation reactions are commonly performed in the presence of a base such as tertiary alkylamines. Preferred bases for the invention are triethylamine and Hünig's base. Most preferably, Hünig's base is used. Commonly, the reaction is carried out in the presence of an organic solvent such as dichloromethane (DCM), acetone or THF. It is preferred to use DCM as solvent. Usually DMSO is used in an over-stoichiometric amount. Sometimes DMSO is also used as solvent. It is preferred to use 1.0-20.0 eq. of DMSO. More preferably 2.0-10 eq. and most preferably, 3.0-4.0 eq. of DMSO are used. Usually, also the activating agent is used in an over-stoichiometric amount. It is preferred to use 1.0-10.0 eq. of oxalyl chloride. More preferably, 1.0-5.0 eq. and most preferably, 1.0-2.0 eq. of oxalyl chloride are used. Usually, such oxidation reactions are performed at −100° C.-0° C. Preferably, the reaction is performed at −80° C.-0° C., more preferably at −50° C.-0° C., and most preferably at −30° C.-0° C.

According to a preferred embodiment, the present invention is therefore directed to a process for preparing a prostaglandin or prostaglandin analog as disclosed above, wherein the oxidation according to step (a) is carried out using DMSO or DMSO in combination with an activating agent selected from oxalyl chloride, $SO_3$.pyridine, DCC, EDC.HCl, and trifluoroacetic anhydride as an oxidizing agent.

As the resulting aldehyde of formula 18 is known to be labile it is preferred to not isolate the compounds of formula 18 but process them in solution as soon as possible. If necessary, it is preferred to store a solution of compounds of formula 18 at −20° C.-0° C., in order to minimize any decomposition.

The process as disclosed above further comprises step (b).

According to step (b), the compound of formula 18 is reacted with a compound of formula 19 in a Wittig reaction of to obtain a compound of formula 20

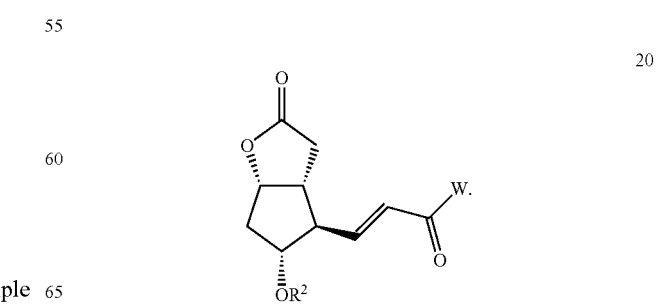

Suitable compounds of formula 19 are known to the person skilled in the art. According to the present invention, any suitable phosphonate might be used. Preferably, a compound of general formula 19,

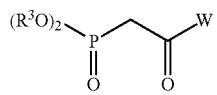

19 is used, wherein W is defined as above and $R^3$ is $C_1$-$C_6$ alkyl or $C_7$-$C_{16}$ aralkyl wherein the aryl group is optionally substituted.

The reaction according to step (b) is carried out in the presence of a salt and a base, to give compounds of the formula 20,

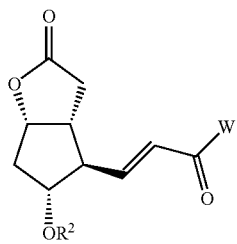

20 wherein W and $R^2$ are defined as above.

Preferably, the reaction according to step (b) is carried out in the presence of an alkali- or an alkaline earth metal salt, and a base. Preferably, alkali metal salts, more preferably lithium salts and most preferably lithium chloride is used. Further, it is preferred to use an organic base. More preferably, tertiary alkylamines such as triethylamine, DBU, and Hünig's base are used. Most preferably, Hünig's base is used. The reaction is carried out at −50° C.-50° C., preferably at −30° C.-30° C. and most preferably at −20° C.-20° C. Suitable solvents for this reaction include toluene, DCM, acetonitrile, DMF, DMSO, THF, and mixtures thereof. Most preferably, the reaction is performed in a mixture of DCM and acetonitrile.

According to the present invention, the product obtained might be purified by any suitable method. It is further preferred to purify the desired compounds of formula 20 by crystallization.

The process as disclosed above also comprises step (c).

According to step (c), the compound of formula 20 is subjected to a reduction to obtain a compound of formula 21

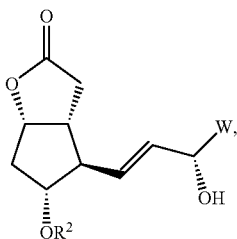

21 wherein W and $R^2$ are defined as above.

According to the present invention, any suitable method comprising the reduction of the oxo group in the side chain of compounds of the formula 20 can be applied for step (c). In particular, compounds of formula 20 are reduced stereoselectively using a chiral reducing agent or a chiral catalyst with an achiral reducing agent to give compounds of the formula 21.

As compounds of the formula 21 are desired as a single isomer suitable reducing agents that give the desired isomer of compounds of formula 21 in high diastereoselectivity are preferred. Such suitable reducing agents are for example borane-dimethylsulfide complex in the presence of a chiral oxazaborolidine catalyst ("Corey-Bakshi-Shibata catalyst"), (−)-B-chlorodiisopinocamphenylborane, or lithium 1,1'-binaphthyl-2,2'-dioxyaluminium hydride. Most preferably, (−)-B-chlorodiisopinocamphenylborane is used. It is preferred to use 1.0-4.0 eq. of (−)-B-chlorodiisopinocamphenylborane. The reaction is usually carried out in the presence of an organic solvent such as diethyl ether, diisopropyl ether, methyl tert-butyl ether (MTBE), THF, 1,2-dimethoxyethane, toluene, hexane, heptane, DCM, or mixtures thereof. It is preferred to use a mixture of THF and heptane. The reaction is carried out at −100° C.-30° C., preferably, at −80° C.-0° C., most preferably, at −40° C.--20° C.

If desired, the unwanted 15R-isomer can be removed by column chromatography at this stage.

According to the present invention, the product obtained might be purified by any suitable method. It is preferred to purify the desired compounds of formula 21 by crystallization and remove traces of 15R-isomer at a later stage.

In case the residue $R^6$ represents H, the process to obtain the compound of general formula (I) comprises an additional step, in particular a deprotection step. Preferably, the compound of formula (I) is obtained by a process comprising the steps (a) oxidation of a compound of general formula 17

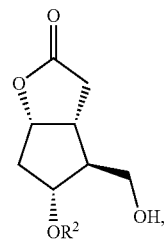

17 to obtain a compound of general formula 18,

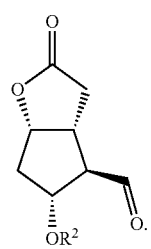

18

(b) Wittig reaction of the compound of formula 18 to obtain a compound of formula 20

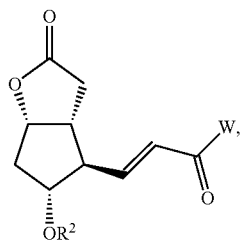

20

(c) reduction of the compound of formula 20 to obtain a compound of formula 21

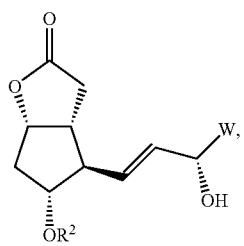

21

(d) deprotection of the compound of formula 21 to obtain a compound of formula 22

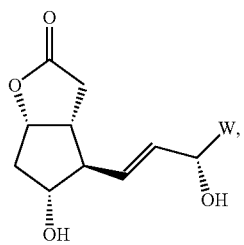

22 wherein W and $R^2$ are defined as disclosed above.

In case residue $R^6$ represents a hydrogen in general formula (I), the process for preparing the compound of formula (I) comprises step (d).

According to step (d), the compound of formula 21 is deprotected to obtain a compound of formula 22

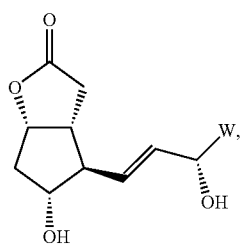

22 wherein W is defined as above.

According to the present invention, any suitable method can be used for step (d). Suitable procedures for deprotection of hydroxyl protecting groups are listed for example in T. W. Greene, "*Protective Groups in Organic Chemistry*", John Wiley & Sons, New York (1981). If carboxylic acids are used as hydroxyl protecting groups, it is preferred to run the deprotection in the presence of an inorganic or organic base. Preferred bases are alkali metal alkoxides, hydroxides, carbonates, and bicarbonates.

Therefore, the present invention relates to a process for preparing a prostaglandin or prostaglandin analog as disclosed above, wherein $R^6$ represents $R^2$ and the compound of formula (I) is obtained by a process comprising the steps (a) oxidation of a compound of general formula 17,

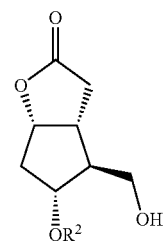

17 to obtain a compound of general formula 18,

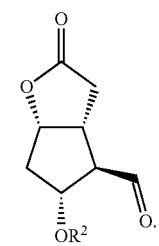

18

(b) Wittig reaction of the compound of formula 18 to obtain a compound of formula 20

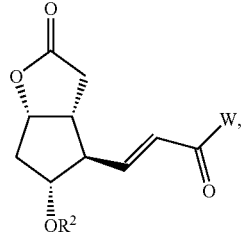

20

(c) reduction of the compound of formula 20 to obtain a compound of formula 21

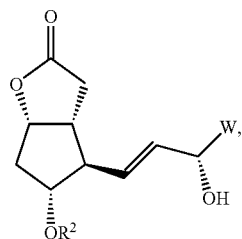

21 wherein W and $R^2$ are defined as disclosed above.

According to one embodiment, the present invention thus relates to a process comprising steps (a), (b), (c), and (i).

The present invention furthermore relates to a process for preparing a prostaglandin or prostaglandin analog as disclosed above comprising the steps (a) oxidation of a compound of general formula 17,

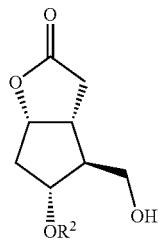

17 to obtain a compound of general formula 18,

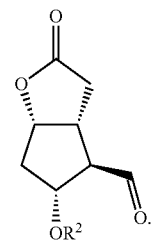

18

(b) Wittig reaction of the compound of formula 18 to obtain a compound of formula 20

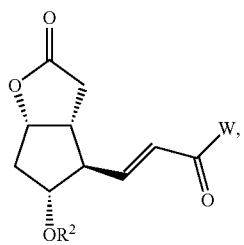

20

(c) reduction of the compound of formula 20 to obtain a compound of formula 21

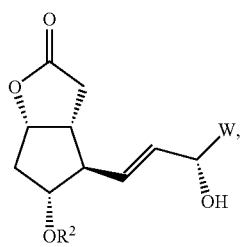

21

(i) reduction of a compound of general formula 21 under transfer hydrogenation conditions to obtain a compound of general formula (II)

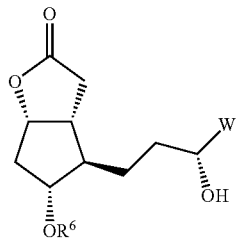

(II)

wherein
W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;
$R^6$ represents $R^2$ with $R^2$ being a hydroxyl protecting group.

According to a further embodiment, the present invention therefore relates to a process for preparing a prostaglandin or prostaglandin analog as disclosed above, wherein $R^6$ represents H and the compound of formula (I) is obtained by a process comprising the steps (a) oxidation of a compound of general formula 17

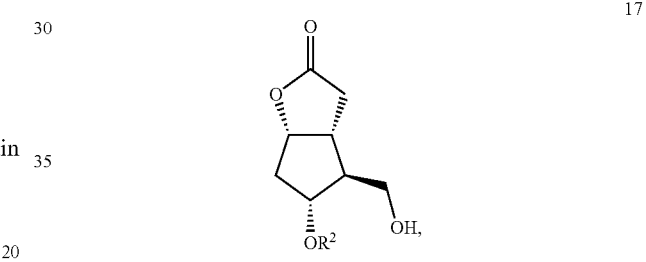

17 to obtain a compound of general formula 18,

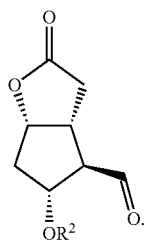

18

(b) Wittig reaction of the compound of formula 18 to obtain a compound of formula 20

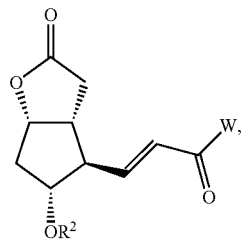

20

(c) reduction of the compound of formula 20 to obtain a compound of formula 21

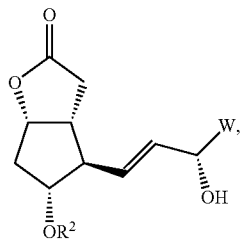

21

(d) deprotection of the compound of formula 21 to obtain a compound of formula 22

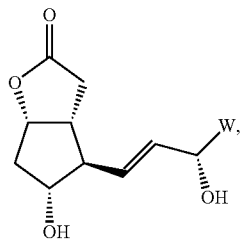

22 wherein W and R² are defined as disclosed above.

Thus, the present invention also relates to a process comprising steps (a), (b), (c), (d), and (i). The present invention therefore relates to a process for preparing a prostaglandin or prostaglandin analog as disclosed above comprising the steps (a) oxidation of a compound of general formula 17,

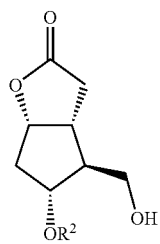

17 to obtain a compound of general formula 18,

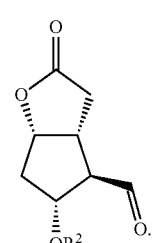

18

(b) Wittig reaction of the compound of formula 18 to obtain a compound of formula 20

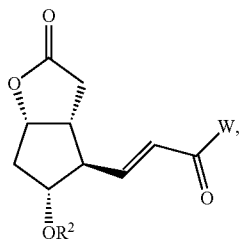

20

(c) reduction of the compound of formula 20 to obtain a compound of formula 21

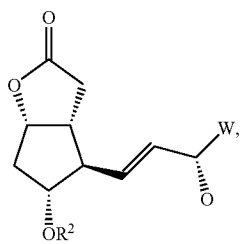

21

(d) deprotection of the compound of formula 21 to obtain a compound of formula 22

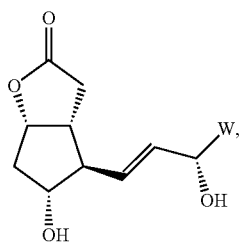

22

(i) reduction of a compound of general formula 22 under transfer hydrogenation conditions to obtain a compound of general formula (II)

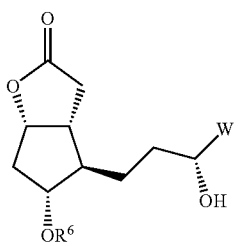

(II)

wherein
W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^2$ represents a hydroxyl protecting group;

$R^6$ represents H.

The process according to the present invention can also comprise further steps after step (i). Preferably, the prostaglandin or prostaglandin analog is obtained by a process, comprising the additional steps (w) to (z) or (x) to (z).

In case the residue $R^6$ in formula (II) represents $R^2$, the process preferably additionally comprises the steps (w) deprotection of the compound of general formula (II) to obtain a compound of general formula 23

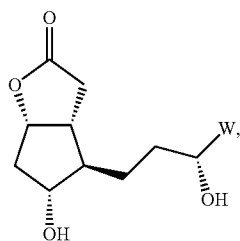

(x) reduction of the compound of formula 23 to obtain a compound of formula 24

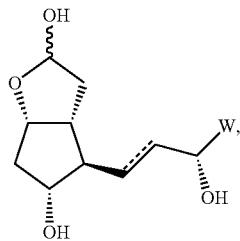

(y) Wittig reaction of the compound of formula 24 to obtain a compound of formula 25

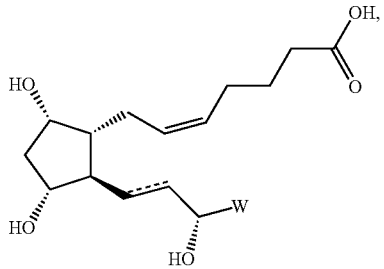

(z) derivatisation of the compound of general formula 25, wherein W, $R^2$ are defined as disclosed above and ----- represents a single bond.

In case the residue $R^6$ in formula (II) represents H, the process preferably additionally comprises the steps (x) reduction of the compound of formula (II) to obtain a compound of formula 24

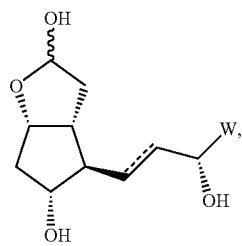

(y) Wittig reaction of the compound of formula 24 to obtain a compound of formula 25

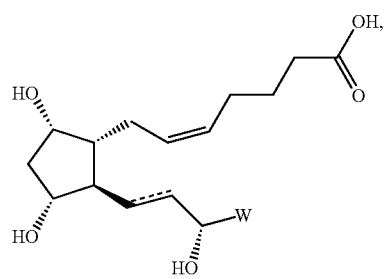

(z) derivatisation of the compound of general formula 25, wherein W is defined as disclosed above and ----- represents a single bond.

According to step (w), the compound of general formula (II) is deprotected to obtain a compound of general formula 23

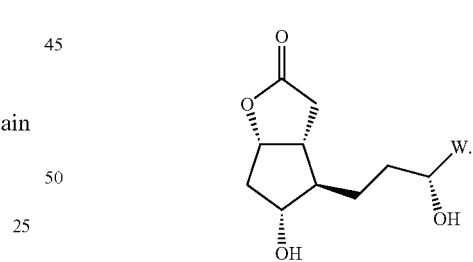

The deprotection is carried out according to any suitable method known to the person skilled in the art. Suitable procedures for deprotection of hydroxyl protecting groups are listed for example in T. W. Greene, "*Protective Groups in Organic Chemistry*", John Wiley & Sons, New York (1981). If carboxylic acids are used as hydroxyl protecting groups, it is preferred to run the deprotection in the presence of an inorganic or organic base. Preferred bases are alkali metal alkoxides, hydroxides, carbonates, and bicarbonates.

The process also comprises step (x). According to step (x), the compound of formula 23 is reduced to obtain a compound of formula 24

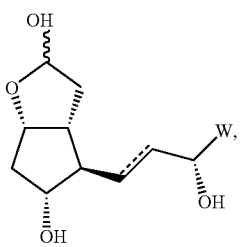

24 wherein W is defined as above and ----- represents a single bond.

Step (x) comprises the reduction of the lactone moiety of compounds of the formula 23.

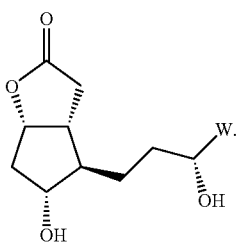

23

The preferred reducing agent for this process is di-isobutylaluminum hydride (DIBAL). It is preferred to perform the reaction in an inert aprotic organic solvent including toluene, hexane, heptane, THF, MTBE, or mixtures thereof. More preferably, a mixture of THF and toluene is used. It is further preferred to run the reaction at −100° C.−−20° C., more preferably, at −90° C.−−40° C., and most preferably, at −80° C.−−50° C.

According to the present invention, the product obtained might be purified by any suitable method. It is preferred to purify and isolate compounds of formula 24 by crystallization.

According to step (y), the compound of formula 24 is reacted with a suitable compound, in particular a compound of formula 26 in a Wittig reaction to obtain a compound of formula 25

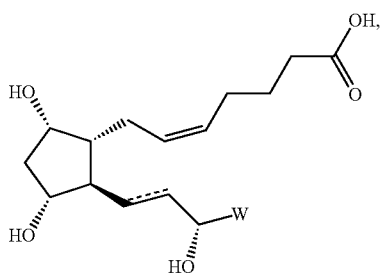

25 wherein W is defined as above and ----- represents a single bond.

Compounds of formula 24 are coupled in a Wittig reaction with a suitable ylide, the ylide being formed by reaction of a compound of the formula 26

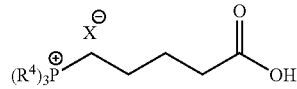

26 wherein $R^4$ represents $C_{1-6}$ alkyl or $C_{6-10}$ aryl and X represents a halogen.

The reaction according to step (y) is generally carried out in the presence of a base.

Preferably, $R^4$ is phenyl and X is bromo. Preferred bases for the formation of the ylide include organolithium reagents including butyllithium, hexyllithium, and heptyllithium, metal amides such as sodium amide, metal hydrides such as sodium hydride, alkali metal alkoxides including sodium methoxide, sodium ethoxide, potassium ethoxide, and potassium tert-butoxide. More preferred bases are alkali metal alkoxides, and most preferably potassium tert-butoxide is used. It is preferred to run the reaction in an inert aprotic organic solvent including toluene, hexane, heptane, THF, MTBE, or mixtures thereof. Most preferably, THF is used. It is preferred to use 3.0 to 15.0 eq. of phosphonium halide relative to the amount of compounds of the formula 24, more preferably, 5.0-10.0 eq. are used. It is further preferred to use 3.0 to 30.0 eq. of base relative to the amount of compounds of the formula 24, more preferably, 5.0-15.0 eq. are used. It is preferred to run the reaction at −20° C.-20° C.

Compounds of the formula 25 can be isolated and purified by methods know to a person skilled in the art but it is preferred not to isolate compounds of formula 25 but use them in solution as obtained after work-up for the next step.

The process as disclosed above also comprises step (z). According to step (z), the compound of general formula 25 is derivatised to give the desired prostaglandins of formula 16. According to the present invention, the term derivatisation means any suitable formation of a derivative of the acid function, for example formation of an ester or an amide.

Preferably, step (z) is an esterification.

Preferably, according to step (z), the compound of formula 25 is subjected to a reaction with an $C_1$-$C_6$ alkyl halide in the presence of a base to obtain compounds of the formula 16. Preferred bases are tertiary amines including triethyl amine, DBU, and Hünig's base; alkali metal alkoxides, hydroxides, carbonates, and bicarbonates. More preferably alkai metal carbonates are used, potassium carbonate being the most preferred base. It is preferred to perform the reaction in an polar aprotic organic solvent including DMF, DMSO, and NMP. More preferably, DMF is used. The reaction is run at temperatures of 20° C.-100° C., more preferably at 30° C.-80° C., and most preferably, at 40° C.-60° C.

The process of the present invention thus might comprise the additional steps (w), (x), (y), and (z) or (x), (y), and (z).

According to a further embodiment, the present invention therefore relates to a process for preparing a prostaglandin or prostaglandin analog as disclosed above, wherein $R^6$ represents $R^2$ and the process additionally comprises the steps (w) deprotection of the compound of general formula (II) to obtain a compound of general formula 23

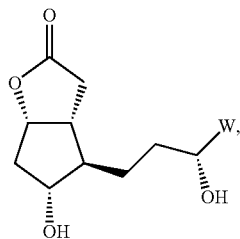

23

(x) reduction of the compound of formula 23 to obtain a compound of formula 24

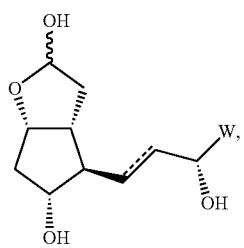

24

(y) Wittig reaction of the compound of formula 24 to obtain a compound of formula 25

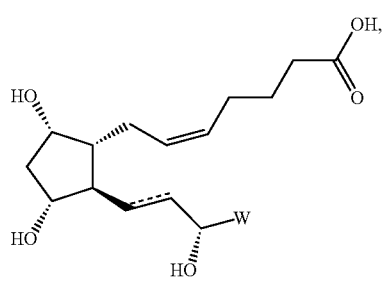

25

(z) derivatisation of the compound of general formula 25, wherein W, $R^2$ and ----- are defined as disclosed above.

The present invention thus relates to a process comprising steps (i), (w), (x), (y), and (z), in particular to a process comprising steps (a), (b), (c), (i), (w), (x), (y), and (z).

According to one embodiment, the present invention also relates to a process for preparing a prostaglandin or prostaglandin analog at least comprising the steps:

(i) reduction of a compound of general formula (I)

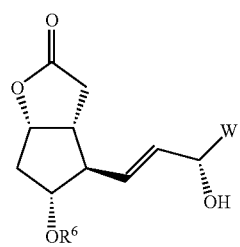

(I)

under transfer hydrogenation conditions to obtain a compound of general formula (II)

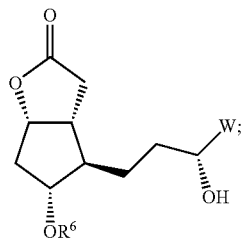

(II)

(w) deprotection of the compound of general formula (II) to obtain a compound of general formula 23

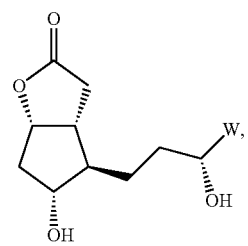

23

(x) reduction of the compound of formula 23 to obtain a compound of formula 24

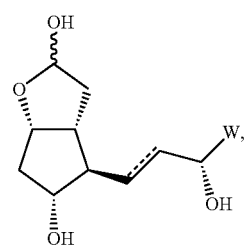

24

(y) Wittig reaction of the compound of formula 24 to obtain a compound of formula 25

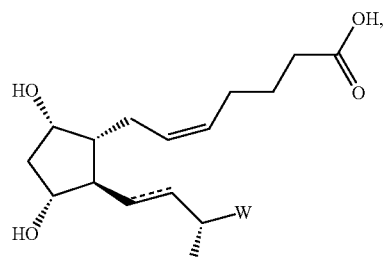

25

(z) derivatisation of the compound of general formula 25, wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents $R^2$ with $R^2$ being a hydroxyl protecting group, and

----- represents a double bond or a single bond.

According to a further embodiment, the present invention relates to a process for preparing a prostaglandin or prostaglandin analog as disclosed above comprising the steps (a) oxidation of a compound of general formula 17,

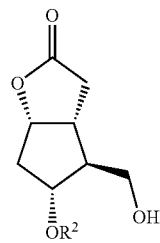

17 to obtain a compound of general formula 18,

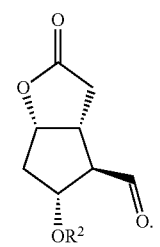

18

(b) Wittig reaction of the compound of formula 18 to obtain a compound of formula 20

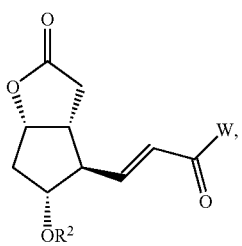

20

(c) reduction of the compound of formula 20 to obtain a compound of formula 21

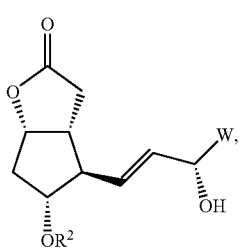

21

(i) reduction of a compound of general formula 21 under transfer hydrogenation conditions to obtain a compound of general formula (II)

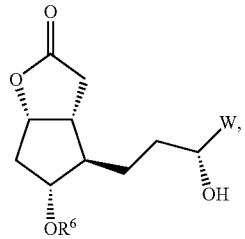

(II)

(w) deprotection of the compound of general formula (II) to obtain a compound of general formula 23

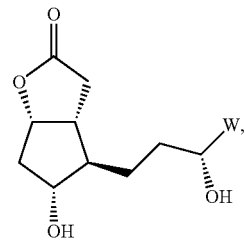

23

(x) reduction of the compound of formula 23 to obtain a compound of formula 24

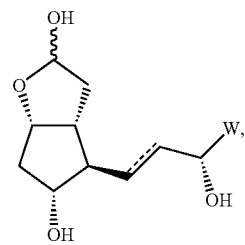

24

(y) Wittig reaction of the compound of formula 24 to obtain a compound of formula 25

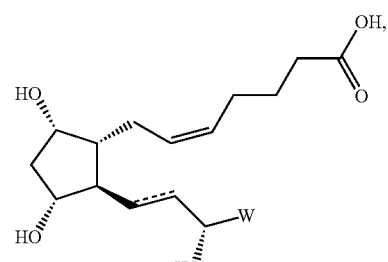

25

(z) derivatisation of the compound of general formula 25, wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_nOR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents $R^2$ with $R^2$ being a hydroxyl protecting group, and

----- represents a double bond or a single bond.

According to a further embodiment, the present invention relates to a process for preparing a prostaglandin or prostaglandin analog as disclosed above, wherein $R^6$ represents H and the process additionally comprises the steps (x) reduction of the compound of formula (II) to obtain a compound of formula 24

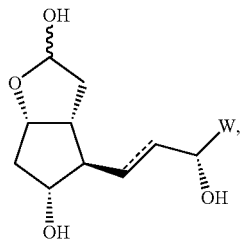

24

(y) Wittig reaction of the compound of formula 24 to obtain a compound of formula 25

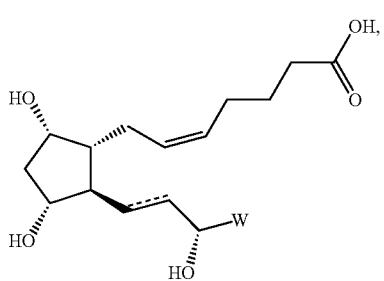

25

(z) derivatisation of the compound of general formula 25, wherein W and ----- are defined as disclosed above.

The present invention also relates to a process comprising steps (i), (x), (y), and (z), in particular to a process comprising steps (a), (b), (c), (d), (i), (x), (y), and (z).

The present invention thus relates to a process for preparing a prostaglandin or prostaglandin analog at least comprising the steps:

(i) reduction of a compound of general formula (I)

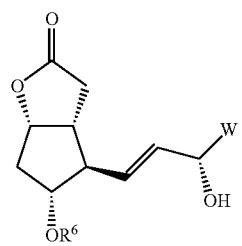

(I)

under transfer hydrogenation conditions to obtain a compound of general formula (II)

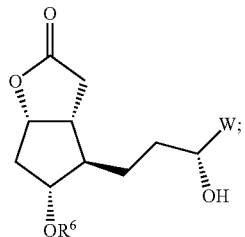

(II)

(x) reduction of the compound of formula (II) to obtain a compound of formula 24

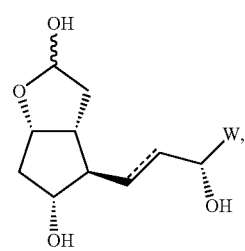

24

(y) Wittig reaction of the compound of formula 24 to obtain a compound of formula 25

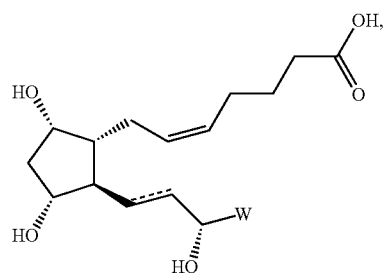

25

(z) derivatisation of the compound of general formula 25, wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_nOR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents H, and

----- represents a double bond or a single bond.

The present invention furthermore relates to a process for preparing a prostaglandin or prostaglandin analog as disclosed above comprising the steps (a) oxidation of a compound of general formula 17,

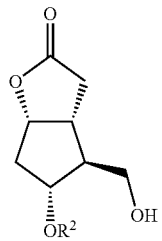

17 to obtain a compound of general formula 18,

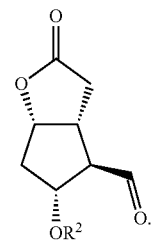

18

(b) Wittig reaction of the compound of formula 18 to obtain a compound of formula 20

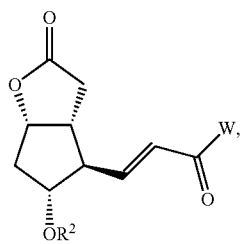

20

(c) reduction of the compound of formula 20 to obtain a compound of formula 21

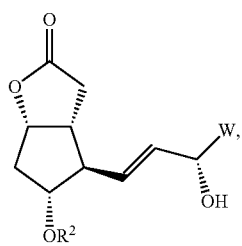

21

(d) deprotection of the compound of formula 21 to obtain a compound of formula 22

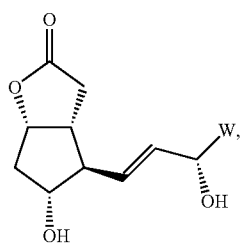

22

(i) reduction of a compound of general formula 22 under transfer hydrogenation conditions to obtain a compound of general formula (II)

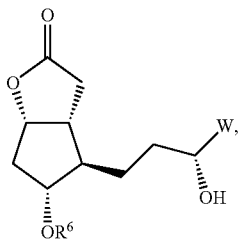

(II)

(x) reduction of the compound of formula (II) to obtain a compound of formula 24

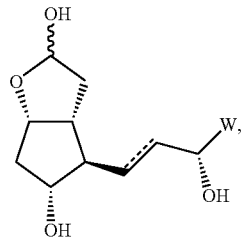

24

(y) Wittig reaction of the compound of formula 24 to obtain a compound of formula 25

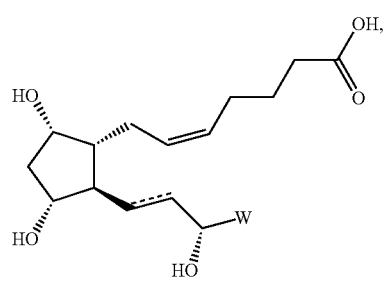

25

(z) derivatisation of the compound of general formula 25, wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;

$R^6$ represents H, and

- - - - - represents a double bond or a single bond.

According to a further embodiment, the present invention is also directed to a process for preparing a prostaglandin or prostaglandin analog consisting of the steps (a), (b), (c), (d), (x), (y), (z), and optionally (i)

(a) oxidation of a compound of general formula 17,

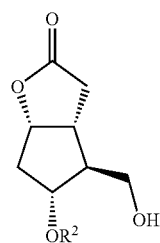

17 to obtain a compound of general formula 18,

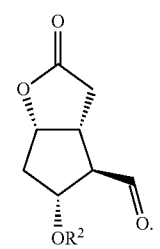

18

(b) Wittig reaction of the compound of formula 18 to obtain a compound of formula 20

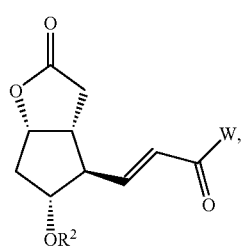

20

(c) reduction of the compound of formula 20 to obtain a compound of formula 21

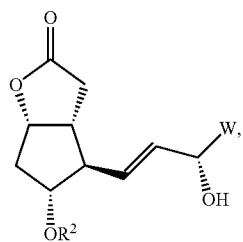

21

(d) deprotection of the compound of formula 21 to obtain a compound of formula 22

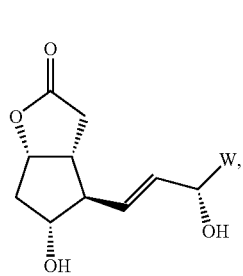

22

(i) reduction of a compound of general formula 22 under transfer hydrogenation conditions to obtain a compound of general formula 23

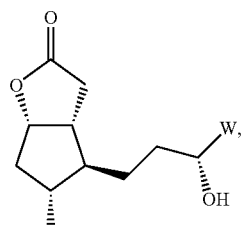

23

(x) reduction of the compound of formula 22 or 23 to obtain a compound of formula 24

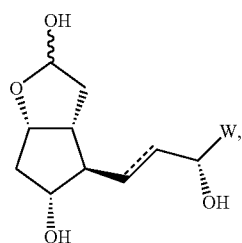

24

(y) Wittig reaction of the compound of formula 24 to obtain a compound of formula 25

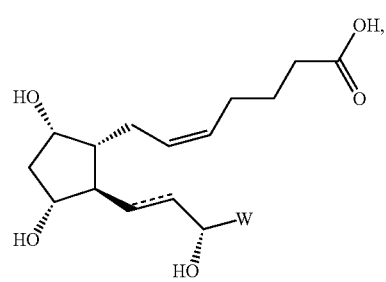

25

(z') derivatisation of the compound of general formula 25 to obtain a compound of general formula 16

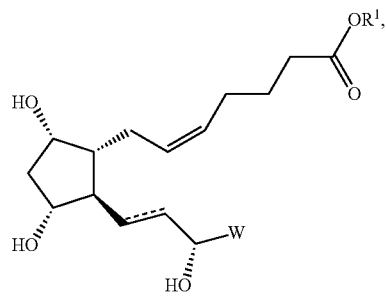

16 wherein
R¹ is selected from $C_1$-$C_6$ alkyl
R² represents a hydroxyl protecting group,
- - - - - represents a double bond or a single bond, and
W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_nOR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$.

With respect to step (z') which is carried out analogously to step (z), reference is made to the above disclosure regarding step (z).

According to a preferred embodiment, the present invention is directed to a process as disclosed above, wherein one or more of the intermediates of general formula 18 or 22 or 23 or 25 is obtained in solution and is used for the subsequent step without further purification.

According to a further embodiment, the present invention relates to a process for preparing a prostaglandin or prostaglandin analog as disclosed above, wherein the prostaglandin is latanoprost.

During step (i) of the process of the present invention, generally a side product of general formula (III) is formed which is preferably removed from the compound of general formula (II):

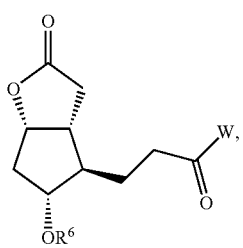

(III)

wherein $R^6$ and W are defined as disclosed above. In the subsequent reduction the keto function of compounds of the formula (III) is reduced more or less unselectively, thus giving rise to additional unwanted 15R-isomer. It is therefore desirable to deplete the side products of formula (III) prior to the next step.

Therefore, the present invention also relates to a compound of general formula (II), which is substantially free of a compound of general formula (III). In the context of the present invention, the term "substantially free" preferably means present in an amount of less than 0.1%.

In case residue $R^6$ represents hydrogen, in step (i) a side product of formula 28 is formed,

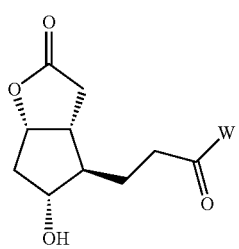

28 wherein W is defined as above. In case residue $R^6$ represents a residue $R^2$, in step (i) a side product of formula 31 is formed,

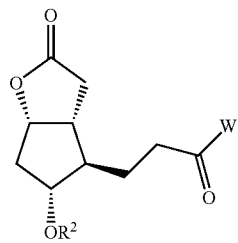

31 wherein W and $R^2$ are defined as above.

For example in the case of latanoprost synthesis, hydrogenation of compound 22a gives compound 28a as a side product.

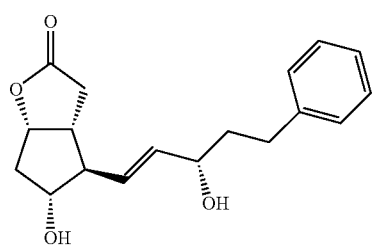

22a

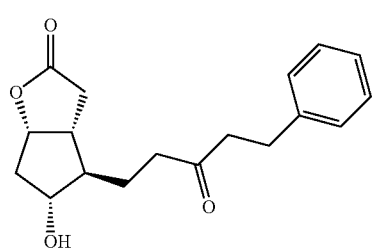

28a

It has been found that compounds of formula (III), in particular compounds of formula 28 or 31 can be removed by selectively transforming compounds of formula (III) into amines or hydrazines of formula (IIIa) and (IIIb) respectively,

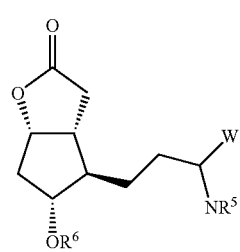

(IIIa)

-continued

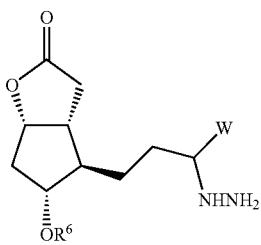
(IIIb)

wherein W and $R^6$ are defined as above and $R^5$ represents an alkyl aryl, or aralkyl moiety, by means of reductive amination. Compounds of general formula (IIIa) and (IIIb) can be removed using acidic extraction.

According to a further embodiment, the present invention therefore relates to a process for preparing a prostaglandin or prostaglandin analog as disclosed above, wherein in step (i), a compound of general formula (III) is formed as a side product:

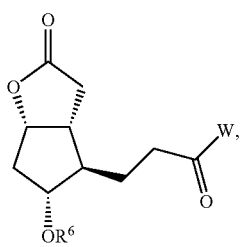
(III)

wherein $R^6$ and W are defined as disclosed above, and the compound of formula (III) is separated from the compound of general formula (II) by a process comprising the steps (1) reductive amination, and (2) acidic extraction.

According to step (1), a reductive amination is carried out. Any suitable method for reductive amination can be used according to the present invention. Step (1) comprises the addition of a primary amine or hydrazine under reductive conditions which selectively react with the keto group of formula (III) to form a secondary amine of formula (IIIa) or the corresponding substituted hydrazine of formula (IIIb).

Said reductive conditions comprise the use of transition metal catalyst under an atmosphere of hydrogen and the use of complex metallic hydrides. Suitable catalyst include Raney nickel and noble metal catalysts such as rhodium, palladium, and platinum. Suitable complex metallic hydrides include sodium borohydride and sodium cyanoborohydride.

According to a further embodiment, the present invention is therefore directed to a process for preparing a prostaglandin or prostaglandin analog as disclosed above, wherein in step (1) a compound of general formula (IIIa) or (IIIb) is formed which is separated from the compound of general formula (II) according to step (2):

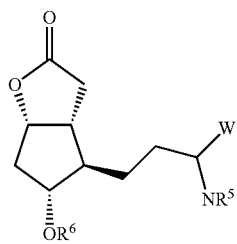
(IIIa)

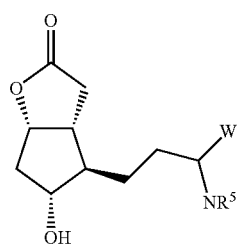
(IIIb)

wherein

W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$, $R^6$ represents hydrogen or $R^2$ with $R^2$ being a hydroxyl protecting group, and $R^5$ represents an alkyl aryl, or aralkyl moiety.

In particular, the present invention relates to a process as disclosed above, wherein in step (1), a compound of general formula 29, 30, 32 or 33 is formed:

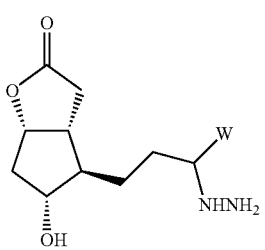
29

30

-continued

32

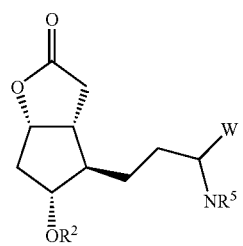

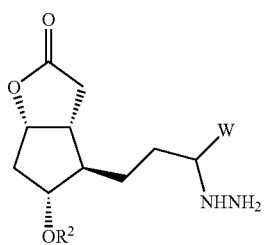

33 wherein W, R² and R⁵ are defined as above.

In case residue R⁶ represents hydrogen, compound of general formula 28 is formed in step (i) which is converted into amines or hydrazines of formula 29 and 30, respectively,

29

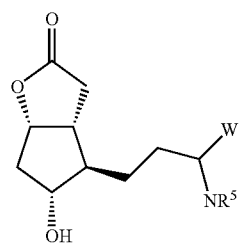

30

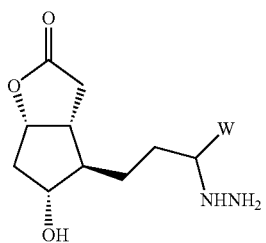

wherein W is defined as above and R⁵ represents an alkyl aryl, or aralkyl moiety.

In case residue R⁶ represents residue R², compound of general formula 31 is formed in step (i) which is converted into amines or hydrazines of formula 32 and 33, respectively,

32

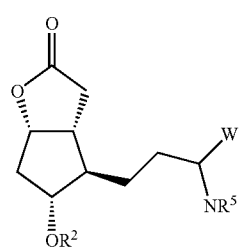

-continued

33

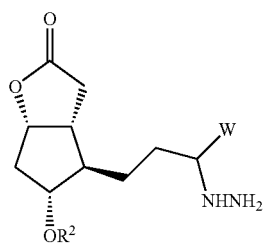

wherein W, R² and R⁵ are defined as above.

According to step (2), acidic extraction is carried out. Any suitable method for acidic extraction can be used in the context of the present invention. Compounds of formula (IIIa) and (IIIb) can easily be removed from compounds of formula (III) by acidic extraction.

The present invention is also directed to a compound of general formula 28a

28a

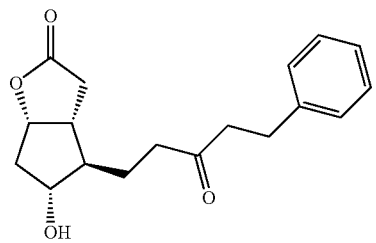

or a compound with the IUPAC name (3aR,4R,5R,6aS)-5-Hydroxy-4-(3-oxo-5-phenyl-pentyl)-hexahydro-cyclopenta[b]furan-2-one.

Furthermore, the present invention also relates to a compound of general formula (IIIa) or (IIIb):

(IIIa)

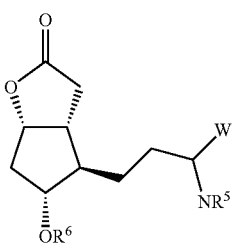

(IIIb)

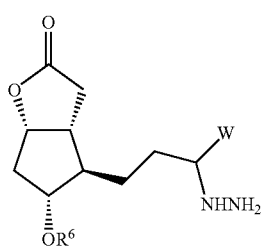

wherein
W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$, $R^6$ represents hydrogen or $R^2$ with $R^2$ being a hydroxyl protecting group, and $R^5$ represents an alkyl aryl, or aralkyl moiety.

In particular, the present invention also relates to a compound selected from compounds of general formula 29, 30, 32 or 33:

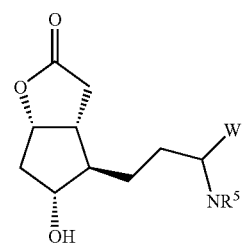

29

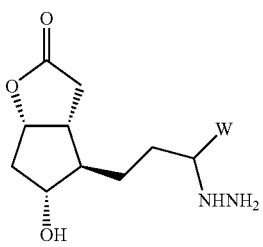

30

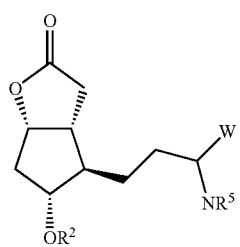

32

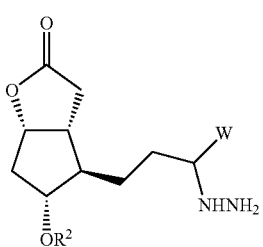

33 wherein W, $R^2$ and $R^5$ are defined as above.

According to a preferred embodiment, the present invention therefore relates to a process for preparing a prostaglandin or prostaglandin analog as disclosed above, wherein the prostaglandin is latanoprost.

However, other prostaglandins or prostaglandin analogs can be prepared using the process of the present invention.

It is also possible to prepare prostaglandins or prostaglandin analogs of general formula 16,

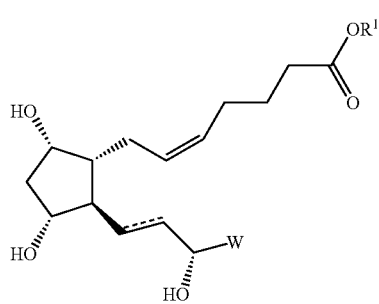

16 wherein $R^1$ is selected from $C_1$-$C_6$ alkyl; W is selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_nOR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$; and ----- represents a double bond.

The present invention also relates to a process for preparing prostaglandins or prostaglandin analogs which do not comprise step (i). In particular, the present invention relates to a process comprising steps (a), (b), (c), (d), (x'), (y), and (z) as disclosed above.

Therefore, according to one embodiment, the present invention relates to a process for preparing a prostaglandin or prostaglandin analog as disclosed above comprising the steps (a) oxidation of a compound of general formula 17,

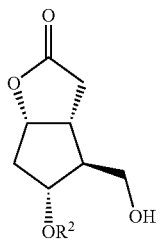

17 to obtain a compound of general formula 18,

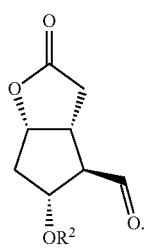

18

(b) Wittig reaction of the compound of formula 18 to obtain a compound of formula 20

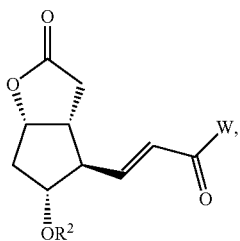
20

(c) reduction of the compound of formula 20 to obtain a compound of formula 21

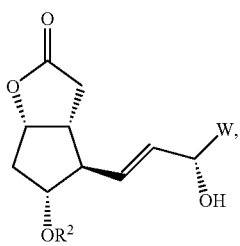
21

(d) deprotection of the compound of formula 21 to obtain a compound of formula 22

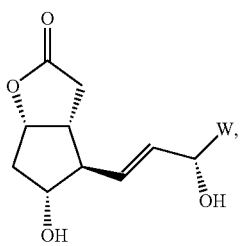
22

(x') reduction of the compound of formula 22 to obtain a compound of formula 24

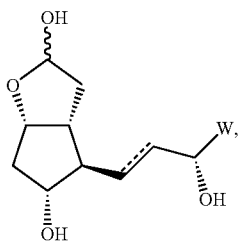
24

(y) Wittig reaction of the compound of formula 24 to obtain a compound of formula 25

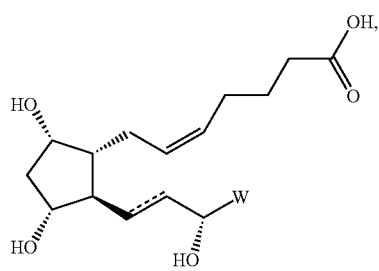
25

(z) derivatisation of the compound of general formula 25, wherein
W represents a residue selected from the group consisting of substituted and unsubstituted $C_1$-$C_6$ alkyl $C_7$-$C_{16}$ aralkyl wherein the aryl group is optionally substituted with one to three substituents selected from the group consisting of $C_1$-$C_6$ alkyl halo and $CF_3$, and $(CH_2)_nOR^a$ wherein n is from 1 to 3 and $R^a$ represents a $C_6$-$C_{10}$ aryl group which is optionally substituted with one to three substituents selected from the group consisting of $C_1$-$C_6$ alkyl halo and $CF_3$;
$R^2$ represents hydroxyl protecting group, and
----- represents a double bond.

With respect to steps (a), (b), (c), (d), (y), and (z), reference is made to the above mentioned embodiments.

Step (x') of the process can be carried out analogously to step (x) as disclosed above. According to step (x'), the compound of formula 22 is reduced to obtain a compound of formula 24

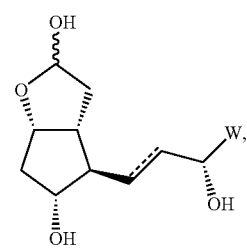
24 wherein W is defined as above and ----- represents a double bond.

Step (x') comprises the reduction of the lactone moiety of compounds of the formula 22.

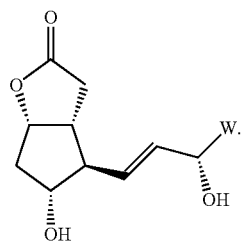
22

The preferred reducing agent for this process is di-isobutylaluminum hydride (DIBAL). It is preferred to perform the reaction in an inert aprotic organic solvent including toluene, hexane, heptane, THF, MTBE, or mixtures thereof. More preferably, a mixture of THF and toluene is used. It is further preferred to run the reaction at −100° C.-−20° C., more preferably, at −90° C.-−40° C., and most preferably, at −80° C.-−50° C.

According to the present invention, the product obtained might be purified by any suitable method. It is preferred to purify and isolate compounds of formula 24 by crystallization.

The process as disclosed above is particularly suitable for the preparation of travoprost.

According to a further embodiment, the present invention therefore relates to a process for preparing a prostaglandin or prostaglandin analog as disclosed above, wherein the prostaglandin is travoprost.

The present invention relates to the novel compounds of formula 28a, 29, 30, 32, and 33 which are intermediates of the process of the present invention.

28a
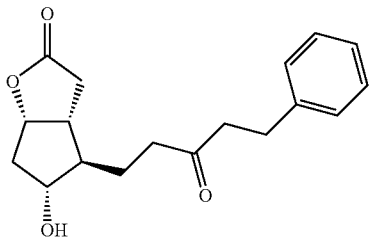

29
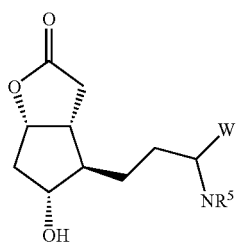

30
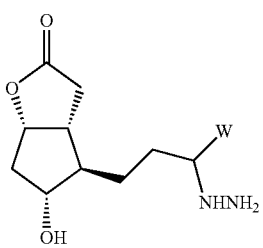

32
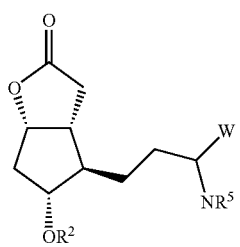

33
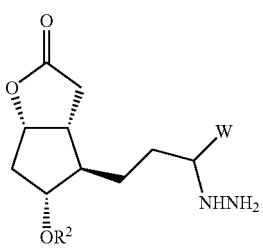

The invention further relates to a novel compound 24b and its use for the preparation of travoprost.

24b
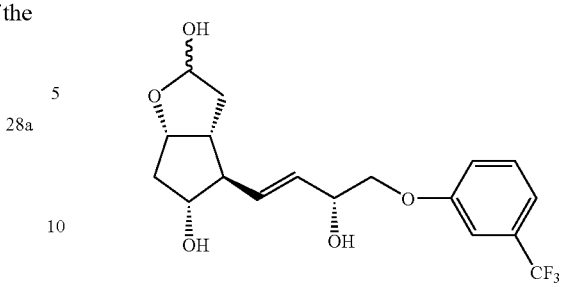

It is obvious to a person skilled in the art that the process of this invention can be applied to the preparation of prostaglandin or prostaglandin analogs like for example latanoprost and travoprost on an industrial scale.

Unless otherwise noted, all %-values in the present application are given as % by weight.

EXAMPLES

The following examples describe the present invention in detail, but they are not to be construed to be in any way limiting for the present invention.

All examples were carried out under an atmosphere of nitrogen if necessary.

Example 1

(2-oxo-4-phenyl-butyl)-phosphonic acid dimethyl ester (19a; $R^3$=Me, W=—$CH_2CH_2$Ph)

To a solution of 68 g of methyl-phosphonic-acid dimethyl ester (MW=124.8; 1.6 eq.) in 325 mL of THF was added 218 mL of n-hexyllithium (2.5M in hexane; 1.6 eq.) at −80° C. The mixture was stirred for 30 min and a solution of 60 g of ethyl-3-phenyl propionate (MW=178.23, d=1.01, 1.0 eq.) in 90 mL of THF was added. The mixture was allowed to warm to ambient temperature and 150 mL of water were added. After separation of the layers the organic layer was extracted twice with water. The pH value of the combined aqueous layers was adjusted to pH=2 with 5M HCl and then extracted twice with DCM. Removal of the organic solvents under reduced pressure gave 89 g of the title compound (Assay: 86.8%; Yield=89.7%). It is not necessary to dry to completion, a 50 w % solution in MED is also suitable for the next step.

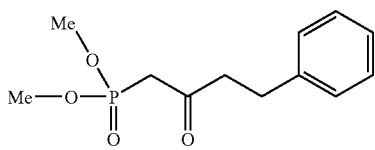 [SMILES: COP(=O)(CC(=O)CCc1ccccc1)OC]

$^1$H-NMR (CDCl$_3$, 300 MHz) δ(ppm)=2.95 (m, CH$_2$, 4H), 3.10 (d, CH$_2$, 2H, J 22.7 Hz), 3.75 (s, CH$_3$, 3H), 3.79 (s, CH$_3$, 3H), 7.30 (m, CH, 5H).

$^{13}$C-NMR (CDCl$_3$, 75.47 MHz) δ(ppm)=29.79, 40.98, 42.68, 45.94, 53.44, 53.53, 126.58, 128.70, 128.87, 128.89, 140.94, 201.30.

Example 2

Benzoic acid (3aR,4R,5R,6aS)-2-oxo-4((E)-3-oxo-5-phenyl-pent-1-enyl)-hexahydro-cyclopenta[b]furan-5yl ester (20a, R²=Bz, W=—CH₂CH₂Ph)

To a solution of 14 mL of oxalyl chloride (COCl)₂ (MW=126.9; 1.50 eq.) in 300 mL of DCM was added a mixture of 29 mL of DMSO (MW=78.1; 3.75 eq.) and 60 mL of DCM at −25° C. The resulting mixture was stirred for 15 min and then a solution of 30 g of benzoyl protected Corey alcohol (17a, R²=Bz; MW=276.29; 1.0 eq.) in 110 mL of DCM was added slowly. Then 84 mL of Hünig's base (MW=129.25; d=0.755; 4.5 eq.) were added and the resulting mixture was stirred for 30 min. Then the reaction mixture is poured onto a stirred, pre-cooled (0° C.) solution of 625 mL of water and 20 mL of glacial acetic acid (MW=60.05, d=1.05; 3.2 eq.) and stirred for another 10 min at 0° C. After separation of the layers the organic layer was washed once with an aqueous NaHCO₃ solution (8.6%) and dried by addition of 6.8 mL of N,O-bis-trimethylsilylacetamide (MW=203.43, d=0.83; 0.25 eq.) at −5° C. to give 520 mL of an organic layer containing benzoyl protected Corey aldehyde (18a, R²=Bz), which was kept at −5° C. prior to further processing.

To a suspension of 21 g of LiCl (MW=42.39; 4.4 eq.) in 280 mL of acetonitrile was added 37 g of compound 19a (MW=256.25; 1.3 eq.; prepared as described in example 1). The resulting mixture is cooled to −15° C. and 45 mL of Hünig's base (MW=129.25; d=0.755; 3.0 eq.) were added. After stirring for 1 h at −15° C. 520 mL of the benzoyl protected Corey aldehyde solution obtained as described above were added. After stirring for 1 h. 19 mL of glacial acetic acid were added before the reaction mixture was warmed to ambient temperature. The reaction mixture was washed consecutively with an aqueous NaCl solution (18%) and water. Then the main part of the organic solvents were removed by distillation under reduced pressure and pre-warmed (80° C.) ethanol (96%) was added. Then the mixture was distilled under reduced pressure until the desired product started to crystallize from the mixture. The crystals were collected by filtration after cooling the suspension to 0° C. and washed twice with an ice-cold mixture of ethanol/water (1/1) to yield 38 g of the title compound after drying (40° C., 10 mbar; yield=84.7%; assay: 99.2%).

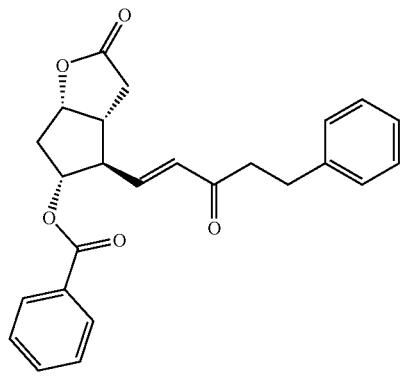 [SMILES: O=C(/C=C/[C@@H]1[C@H]2CC(=O)O[C@H]2C[C@H]1OC(=O)c1ccccc1)CCc1ccccc1]

¹H-NMR (CDCl₃, 300 MHz) δ(ppm)=2.35 (dd, CH₂, 1H, J 10.6 Hz, J 3.1 Hz), 2.60 (m, CH₂, 3H), 2.90 (m, CH, CH₂, 5H), 5.09 (dt, CH, 1H, J 4.3 Hz, 1.8 Hz), 5.33 (q, CH, 1H, J 5.5 Hz), 6.25 (d, CH, 1H, 16.4 Hz), 6.70 (m, CH, 1H), 7.25 (m, CH, 5H), 7.49 (m, CH, 2H), 7.61 (m, CH, 1H), 8.02 (m, CH, 2H).

¹³C-NMR (CDCl₃, 75.47 MHz) δ(ppm)=30.37, 35.28, 38.23, 42.87, 42.95, 54.43, 78.89, 83.54, 126.64, 128.81, 128.95, 129.01, 129.64, 130.11, 131.86, 133.96, 141.29, 143.48, 166.28, 176.26, 199.06.

Example 3

Benzoic acid (3aR,4R,5R,6aS)-4-((E)-(S)-3-hydroxy-5-phenyl-pent-1-enyl)-2-oxo-hexahydro-cyclopenta[b]furan-5-yl ester (21a; R²=Bz, W=—CH₂CH₂Ph)

To a solution of 50 g of compound 20a (MW=406.8; 1.0 eq.; prepared as described in example 2) in 500 mL of dry THF was slowly added 190 mL of (−)-DIP-Cl solution (MW=320.76; 2.75 eq. 63% in heptane) at −30° C. After stirring for 6 h 180 mL of methanol were added and the mixture was warmed to room temperature. After removal of the solvent under reduced pressure, the residue was dissolved in methanol/water (10/1) and extracted twice with heptane. After concentration of the aqueous layer, ethyl acetate was added and the resulting mixture was consecutively extracted with an aqueous NaCl solution (9%) and with an aqueous NaHCO₃ solution (8.6%). The organic solvents were removed under reduced pressure and the residue was recrystallized from ethyl acetate/n-heptane (1/7) to give 41 g of the title compound after drying (40° C., 10 mbar; yield=81.2%, de(S)=89.2%).

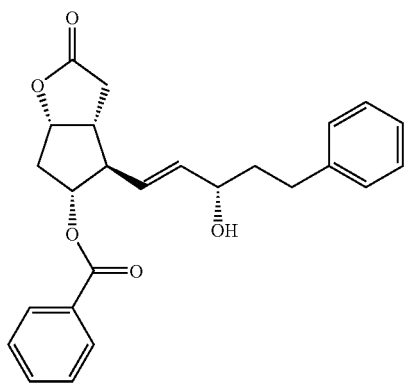 [SMILES: O=C1C[C@@H]2[C@@H](/C=C/[C@@H](O)CCc3ccccc3)[C@H](OC(=O)c3ccccc3)C[C@@H]2O1]

H-NMR (CDCl₃, 300 MHz) δ(ppm)=2.63 (bs, OH, 1H), 2.85 (m, CH₂, 2H), 2.75 (m, CH, CH₂, 7H), 4.17 (t, CH, 1H, J 6.1 Hz), 5.09 (dt, CH, 1H, J 4.3 Hz, 1.8 Hz), 5.29 (q, CH, 1H, J 5.4 Hz), 5.65 (m, CH, 2Hz), 7.23 (m, CH, 5H), 7.45 (m, CH, 2H), 7.60 (m, CH, 1H), 8.02 (m, CH, 2H).

¹³C-NMR (CDCl₃, 75.47 MHz) δ(ppm)=32.00, 35.27, 37.96, 39.08, 43.09, 54.36, 71.82, 79.40, 83.62, 126.38, 128.83, 128.87, 128.97, 129.13, 129.92, 130.07, 133.80, 136.47, 141.96, 166.49, 176.79.

Example 4

(3aR,4R,5R,6aS)-4-((S)-3-Hydroxy-5-phenyl-pentyl)-hexahydro-cyclopenta[b]furan-2,5-diol (24a, W=—CH₂CH₂Ph)

7.55 g of a 30% solution of sodium methylate in methanol (MW=52.02; 0.7 eq.) were added drop wise to a solution of 25 g of compound 21a (MW=406.48; 1 eq.; prepared as described in example 3) in 500 mL of methanol and stirring was continued for 2 h. The resulting reaction mixture was added drop wise to 500 mL of cold water (0-5° C.) and the pH value of the mixture was adjusted to pH=6.5 by addition of 1M HCl. The resulting solution is concentrated under reduced pressure to a volume of approx. 350 mL and 500 mL of MTBE were added. After separation of the layers, the aqueous layer was extracted once with MTBE and the combined organic layers were treated with 1.8 g of methane sulfonic acid. The resulting solution was stirred for 1 h at ambient temperature before 100 mL of brine and 190 mL of 8.6% aqueous $NaHCO_3$ solution were added. After the layers were separated the organic layer was washed once with brine and then concentrated under reduced pressure to a mass of approx. 200 g. Then 380 mL of ethanol were added, and the resulting mixture was again concentrated under reduced pressure to a mass of approx. 40 g. The resulting concentrate is diluted with 215 g of ethanol to give 255 g of a solution of 18.6 g of 22a (W=—$CH_2CH_2Ph$) in ethanol which was directly used in the next step without further purification.

To a suspension of 16.5 g of potassium formate (MW=84.12; 3.2 eq.) and 5.3 g of Pd—C (20%) in 21 mL of water were added 255 g of the ethanolic solution of 22a prepared as described above. After stirring for 1 h at room temperature the suspension was filtered and the solids were washed with ethanol. The combined filtrates were concentrated under reduced pressure to a mass of approx. 50 g. Then 400 mL of water were added and the mixture was concentrated under reduced pressure to a final mass of approx. 350 g. Then 130 g of NaCl and 750 mL of MTBE were added and after separation of the layers the aqueous layer was extracted once with MTBE. The combined organic layers were diluted with toluene, washed with brine and concentrated under reduced pressure to a mass of 150 g. Then the concentrate was diluted with 350 g of toluene and 100 g of THF to give 600 g of a solution of 23a (W=—$CH_2CH_2Ph$) in toluene/THF which was used in the next step without further purification.

600 g of the solution of 23a in toluene/THF prepared as described above were cooled to −70° C. and 195 mL of a 1M solution of DIBAL-H in toluene (3.2 eq.) were added drop wise. Then the reaction was quenched by adding 4 mL of methanol during 1 h at −70° C. The resulting mixture was poured into 2 L of a 1M potassium phosphate buffer (pH=7) at 20° C. and stirring was continued for 1 h. After separation of the layers 830 mL of MTBE and 590 g of NaCl were added to the aqueous layer. After separation of the layers the aqueous layer was extracted twice with MTBE. The combined organic layers were washed with 450 mL of an aqueous NaCl solution (26.5%) and concentrated under reduced pressure to a mass of approx. 285 g. The resulting suspension was stirred at ambient temperature for 30 min and was then cooled to 0° C. and stirred for additional 2 h at this temperature. The crystals were collected by filtration and washed with 30 mL of toluene to give 16.8 g of the title compound after drying (30° C., 10 mbar; yield: 89.9%).

Mp 110-114° C.

$^1$H-NMR (DMSO-d6, 300 Mz) d (ppm)=1.01 (m, 1H), 1.20-1.89 (m, 9H), 1.96-2.2 (m, 2H), 2.19-2.04 (m, 2H), 2.43-2.61 (m, 1H), 2.62-2.76 (m, 1H), 3.41-3.56 (m, 2H), 4.21-4.37 (m, 1H), 4.42 (d, 1H, J 5.4 Hz), 4.61 (d, 0.7H, J 5.8 Hz), 4.79 (d, 0.3H, J 5.8 Hz), 5.30 (t, 0.3H, J 3.7 Hz), 5.38 (t, 0.7H, J 3.7 Hz), 5.82 (d, 0.8H, J 4.4 Hz), 6.12 (d, 0.2H, J 4.4 Hz), 7.10-7.26 (m, 5H).

$^{13}$C-NMR (DMSO-d6, 75.47 Mz) d (ppm)=29.61, 30.10, 32.42, 36.23, 39.51, 39.79, 39.89, 40.06, 40.34, 40.62, 40.80, 40.90, 41.18, 41.77, 41.871 43.76, 45.74, 46.42, 53.28, 54.11, 70.37, 77.62, 77.97, 79.59, 81.63, 99.97, 100.68, 126.35, 129.08, 129.13, 143.46.

Example 5

Latanoprost 16a (W=—$CH_2CH_2Ph$, $R^1$=$O^iPr$)

A suspension of 35 g of (4-carboxybutyl)triphenylphosphonium bromide (MW=443.32; 7.5 eq.) and 95 mL of THF was cooled to 0° C. and 140 g of a 2M solution of potassium-tert butoxide in THF (9.5 eq.) were added drop wise and stirring was continued at 0° C. for 30 min. The resulting suspension was cooled to −17° C. and a solution of 8 g of compound 24a (MW=306.41; 1 eq.; prepared as describe in example 4) in 25 mL of THF was added and the reaction mixture was stirred at −17° C. for 20 h. Then 180 mL of brine were added and the resulting suspension was stirred for 30 min at −10° C. Then the cold suspension was filtered and the filtrate were washed twice with 180 mL of toluene. Then 180 mL of MTBE were added to the aqueous layer and the pH was adjusted to 2.0-1.5 by addition of a solution of sulfamic acid in water (20%). After separation of the layers, the aqueous layer was extracted once with MTBE and the combined organic layers were washed with brine. After separation of the layers the organic layer was concentrated under reduced pressure to a volume of approx. 100 mL. Then 28 g of DMF were added and resulting solution was concentrated under reduced pressure to give 32 g of a solution of 25a (W=—$CH_2CH_2Ph$) in DMF which was used in the next step without further purification.

5.8 g of milled $K_2CO_3$ (MW=138.21; 1.6 eq.) were added to 32 g of the solution of 25a in DMF (prepared as described above). After stirring the resulting suspension for 15 min at ambient temperature, 6.6 g of isopropyliodide (MW=166.99; 1.5 eq.) were added. Then the mixture was heated to 50° C. and stirred for 18 h at this temperature. Then the reaction mixture was diluted with 190 mL of MTBE and 60 mL of water and the pH was adjusted by addition of a solution of sulfamic acid in water (20%) to 2.0-1.5. After separation of the layers the organic layer was washed three times with water and then an aqueous $Na_2CO_3$ solution (8.6%). Finally, the organic layer was washed twice with water and the pH value was adjusted to pH=6.5 by addition of an aqueous citric acid solution (15%). After separation of the layers the organic concentrated under reduced pressure to give 6.9 g of the crude title compound, which was purified by chromatography.

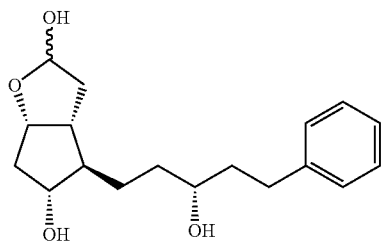

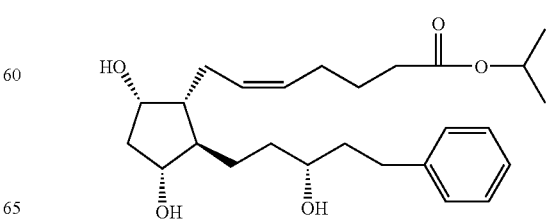

¹H-NMR (CDCl₃, 300 MHz) δ(ppm)=1.26 (d, CH3, 6H, J 6.3 Hz), 1.40 (m, CH₂, 2H), 1.71 (m, CH, CH₂, 9H), 1.90 (s, CH₂, 2H), 2.17 (m, CH₂, 2H), 2.32 (t, CH, 4H, J 7.1 Hz), 2.77 (m, CH, CH₂, 4H), 3.69 (t, CH, 1H, 6.3 Hz), 3.98 (bs, OH, 1H), 4.20 (bs, OH, 1H), 5.03 (q, CH, 1H, J 6.3 Hz), 5.46 (m, CH, 2H), 7.23 (m, CH, 3H), 7.31 (m, CH, 2H).

¹³C-NMR (CDCl₃, 75.47 MHz) δ(ppm)=22.27, 25.37, 27.06, 27.32, 30.06, 32.56, 34.49, 36.24, 39.48, 42.92, 52.30, 53.25, 68.11, 71.73, 75.06, 79.17, 126.24, 128.84, 129.81, 129.98, 142.56, 173.97.

Example 6

(3aR,4R,5R,6aS)-4-((S)-3-Hydroxy-5-phenyl-pentyl)-hexahydro-cyclopenta[b]furan-2,5-diol (24a, W=—CH₂CH₂Ph) via derivatization and extraction of side product 28a 7.55 g of a 30% solution of sodium methylate in methanol (MW=52.02; 0.7 eq.) were added drop wise to a solution of 25 g of compound 21a (MW=406.48; 1 eq.; prepared as described in example 3) in 500 mL of methanol and stirring was continued for 2 h. The resulting reaction mixture was added drop wise to 500 mL of cold water (0-5° C.) and the pH value of the mixture was adjusted to pH=6.5 by addition of 1M HCl. The resulting solution is concentrated under reduced pressure to a volume of approx. 350 mL and 500 mL of MTBE were added. After separation of the layers the aqueous layer was extracted once with MTBE and the combined organic layers were treated with 1.8 g of methane sulfonic acid. The resulting solution was stirred for 1 h at ambient temperature before 100 mL of brine and 190 mL of 8.6% aqueous NaHCO3 solution were added. After the layers were separated the organic layer was washed once with brine and then concentrated under reduced pressure to a mass of approx. 200 g. Then 380 mL of ethanol were added, and the resulting mixture was again concentrated under reduced pressure to a mass of approx. 40 g. The resulting concentrate is diluted with 215 g of ethanol to give 255 g of a solution of 18.6 g of 22a (W=—CH2CH2Ph) in ethanol which was directly used in the next step without further purification.

To a suspension of 16.5 g of potassium formate (MW=84.12; 3.2 eq.) and 5.3 g of Pd—C (20%) in 21 mL of water were added 255 g of the ethanolic solution of 22a prepared as described above. After stirring for 1 h at room temperature the suspension was filtered and the solids were washed with ethanol. The pH of the combined filtrates was adjusted to 6.0 by addition of 6M aqueous HCl and concentrated in vacuo to a mass of 270 g. To the solution were added 65.5 g of ammonium acetate, 33 mL of acetic acid, 5.2 g sodium cyanoborohydride and the resulting mixture was stirred for 20 h at ambient temperature. The reaction mixture (content of sice product 28a<0.1%) was concentrated in vacuo to a mass of approx. 50 g. Then 400 mL of water were added and the distillation was continued to a final mass of approx. 350 g. To the concentrate were added 80 g of sodium chloride and 750 mL of MTBE. After separation of the layers the aqueous layer was extracted with 750 mL of MTBE. The combined organic layers were washed with 375 mL of brine, diluted with 750 mL of toluene, filtered and concentrated in vacuo to a mass of approx. 150 g. Then the concentrate was diluted with 355 g of toluene and 100 g of THF to give 600 g of a solution of 23a (W=—CH₂CH₂Ph) in toluene/THF which was used in the next step without further purification.

600 g of the solution of 23a in toluene/THF prepared as described above were cooled to −70° C. and 195 mL of a 1M solution of DIBAL-H in toluene (3.2 eq.) were added drop wise. Then the reaction was quenched by adding 4 mL of methanol during 1 h at −70° C. The resulting mixture was poured into 2 L of a 1M potassium phosphate buffer (pH=7) at 20° C. and stirring was continued for 1 h. After separation of the layers 830 mL of MTBE and 590 g of NaCl were added to the aqueous layer. After separation of the layers the aqueous layer was extracted twice with MTBE. The combined organic layers were washed with 450 mL of 26.5% aqueous NaCl solution and concentrated under reduced pressure to a mass of approx. 285 g. The resulting suspension was stirred at ambient temperature for 30 min and was then cooled to 0° C. and stirred for additional 2 h at this temperature. The crystals were collected by filtration and washed with 30 mL of toluene to give 14.8 g of the title compound after drying (30° C., 10 mbar; yield: 79.2%).

Example 7

(3aR,4R,5R,6aS)-4-((S)-3-Hydroxy-5-phenyl-pentyl)-hexahydro-cyclopenta[b]furan-2,5-diol (24a, W=—CH₂CH₂Ph)—reversed order of steps A solution of 25.0 g of compound 21a (MW=406.48; 1 eq.; prepared as described in example 3) in 260 mL of ethanol were added to a suspension of 30 g of potassium formate (MW 84.12; 5.8 eq.) and 5.3 g of Pd—C (20%) in 21 mL of water. After stirring for 2.5 h at room temperature the suspension was filtered and washed with 200 mL of ethanol. The pH of the combined filtrates was adjusted to 6.0 by addition of 6M aqueous HCl and ethanol was removed in vacuo. To the resulting concentrate was added 200 mL of water and the mixture was concentrated in vacuo to a mass of 100 g. To the concentrate were added 500 mL of MTBE and after separation of the layers the aqueous layer was extracted twice with 150 mL of MTBE. The combined organic layers were treated with 65 mL of 10M aqueous NaOH. After stirring for 15 min at ambient temperature the reaction mixture was diluted with 30 mL of water and stirring was continued for 3 h. Then the pH of the mixture was adjusted to 1.0 by addition of 12M aqueous HCl and the resulting mixtures was diluted with 500 mL of MTBE. After separation of the layers the aqueous layer was extracted with 150 mL of MTBE. The organic layers were combined and 2.5 g of methane sulfonic acid were added. After stirring the resulting acidic solution for 1 h at room temperature 100 mL of brine were added and the pH was adjusted to 7.0 by addition of an aqueous solution of sodium bicarbonate (8.6%). After separation of the layers the aqueous layer was extracted twice with 150 mL of MTBE. The combined organic layers were diluted with 470 mL of toluene, filtered and concentrated in vacuo to a mass of approx. 150 g. Then the concentrate was diluted with 350 g of toluene and 100 g of THF to give 600 g of a solution of 23a (W=—CH₂CH₂Ph) in toluene/THF which was used in the next step without further purification.

600 g of the solution of 23a in toluene/THF prepared as described above were cooled to −70° C. and 285 mL of a 1M solution of DIBAL-H in toluene (4.6 eq.) were added drop wise. Then the reaction was quenched by adding 4 mL of methanol during 1 h at −70° C. The resulting mixture was poured into 2 L of a 1M potassium phosphate buffer (pH=7) at 20° C. and stirring was continued for 1 h. After separation of the layers 830 mL of MTBE and 530 g of NaCl were added to the aqueous layer. After separation of the layers the aqueous layer was extracted twice with MTBE. The combined organic layers were washed with 450 mL of an aqueous NaCl solution (26.5%) and concentrated under reduced pressure to a mass of approx. 285 g. The resulting suspension was stirred at ambient temperature for 30 min and was then cooled to 0° C. and stirred for additional 2 h at this temperature. The crystals were collected by filtration and washed with 30 mL of toluene to give 15.3 g of the title compound after drying (30° C., 10 mbar; yield: 81.9%).

Example 8

(3aR,4R,5R,6aS)-4-((S)-3-Hydroxy-5-phenyl-pentyl)-hexahydro-cyclopenta[b]furan-2,5-diol (24a, W=—CH$_2$CH$_2$Ph)—reversed order of steps combined with derivatization and extraction of side product 31a (R$^2$=Bz, W=—CH$_2$CH$_2$Ph)

A solution of 25.0 g of compound 21a (MW=406.48; 1 eq.; prepared as described in example 3) in 260 mL of ethanol were added to a suspension of 30 g of potassium formate (MW 84.12; 5.8 eq.) and 5.3 g of Pd—C (20%) in 21 mL of water. After stirring for 2.5 h at room temperature the suspension was filtered and washed with 200 mL of ethanol. The pH of the combined filtrates was adjusted to 6.0 by addition of 6M aqueous HCl and the solution was concentrated in vacuo to a mass of 250 g. To the resulting concentrate 31.6 g of ammonium acetate, 19 mL of acetic acid and 5.2 g of sodium cyanoborohydride were added and the resulting mixture was stirred for 18 h at 35° C. The reaction mixture (content of side product 31a) was diluted with 250 mL of water and ethanol was distilled in vacuo to a final mass of 200 g. The residue was diluted with 50 mL of brine and 500 mL of MTBE and the pH was adjusted to 2.5 by addition of 6M aqueous HCl. The layers were separated to give approx. 500 mL of a solution of 27a (R$^2$=Bz, W=—CH$_2$CH$_2$Ph) in MTBE. To this solution were added 65 mL of 10M aqueous NaOH. After stirring for 15 min at ambient temperature the reaction mixture was diluted with 30 mL of water and stirring was continued for 3 h. Then the pH of the mixture was adjusted to 1.0 by addition of 12M aqueous HCl. The mixture was diluted with 500 mL of MTBE and after separation of the layers the aqueous layer was extracted with 150 mL of MTBE. The combined organic layers were treated with 2.5 g of methane sulfonic acid. After stirring the resulting acidic solution for 1 h at room temperature 125 mL of brine were added and the pH was adjusted to 7.0 by addition of an aqueous solution of sodium bicarbonate (8.6%). After separation of the layers the organic layer was diluted with 470 mL of toluene, filtered and concentrated in vacuo to a mass of approx. 150 g. Then the concentrate was diluted with 350 g of toluene and 100 g of THF to give 600 g of a solution of 23a (W=—CH$_2$CH$_2$Ph) in toluene/THF which was used in the next step without further purification.

600 g of the solution of 23a in toluene/THF prepared as described above were cooled to −70° C. and 285 mL of a 1M solution of DIBAL-H in toluene (4.6 eq.) were added drop wise. Then the reaction was quenched by adding 4 mL of methanol during 1 h at −70° C. The resulting mixture was poured into 2 L of a 1M potassium phosphate buffer (pH=7) at 20° C. and stirring was continued for 1 h. After separation of the layers 830 mL of MTBE and 530 g of NaCl were added to the aqueous layer. After separation of the layers the aqueous layer was extracted twice with MTBE. The combined organic layers were washed with 450 mL of an aqueous NaCl solution (26.5%) and concentrated under reduced pressure to a mass of approx. 285 g. The resulting suspension was stirred at ambient temperature for 30 min and was then cooled to 0° C. and stirred for additional 2 h at this temperature. The crystals were collected by filtration and washed with 30 mL of toluene to give 15.0 g of the title compound after drying (30° C., 10 mbar; yield: 80.3%).

Example 9

Benzoic acid (3aR,4R,5R,6aS)-2-oxo-4-((E)-3-oxo-4-(3-(trifluormethyl)phenoxy)-but-1-enyl)-hexahydro-cyclopenta[b]furan-5yl ester (2ba, R$^2$=Bz, W=—CH$_2$O(m-CF$_3$C$_6$H$_4$))

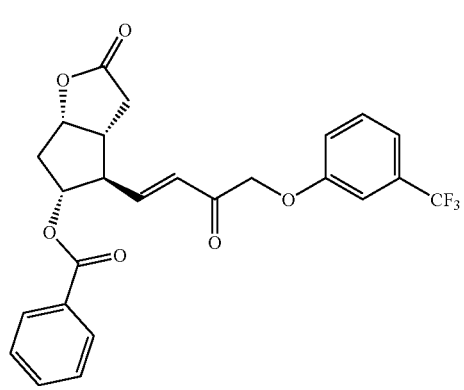

20b

Following a procedure similar to that described in example 2 and using m-CF$_3$C$_6$H$_4$OCH$_2$COCH$_2$PO(OMe)$_2$ as Horner-Emmons-reagent compound 20b was prepared in 79.5% yield.

Example 10

Benzoic acid (3aR,4R,5R,6aS)-4-((E)-(S)-3-hydroxy-4-(3-(trifluormethyl)phenoxy)-but-1-enyl)-2-oxo-hexahydro-cyclopenta[b]furan-5-yl ester (2ba; R$^2$=Bz, W=—CH$_2$O(m-CF$_3$C$_6$H$_4$))

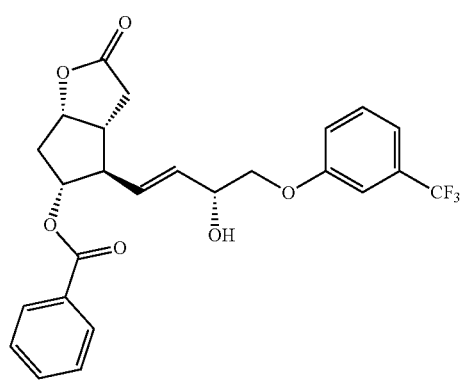

21b

Following a procedure similar to that described in example 3 and using compound 20b as starting material compound 21b was prepared in 80.5% yield (de=88.7%).

Example 11

(3aR,4R,5R,6aS)-4-((R)-3-Hydroxy-4-(3-(trifluormethyl)phenoxy)-but-1-enyl)-hexahydro-cyclopenta[b]furan-2,5-diol (24b, W=—CH$_2$O(m-CF$_3$C$_6$H$_4$))

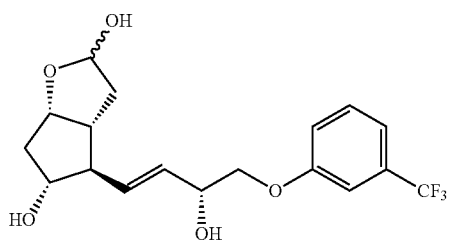

Following a procedure similar to that described in example 4 and using compound 21b as starting material compound 24b was prepared in 81.2% yield.

Example 12

Travoprost 16b (W=—CH$_2$O(m-CF$_3$C$_6$H$_4$), R$^1$=O$^i$Pr)

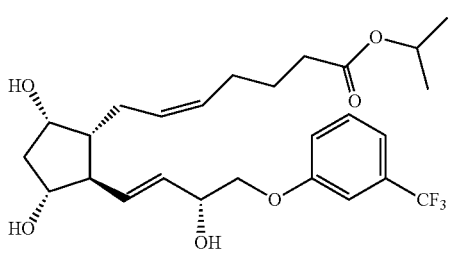

Following a procedure similar to that described in example 5 and using compound 24b as starting material compound 16b was prepared as a colorless oil.

| List of abbreviations: | |
|---|---|
| (-)-DIP-Cl | (-)-B-chlorodiisopinocamphenylborane |
| CBS | Corey-Bakshi-Shibata |
| DBU | 1,8-Diazabicyclo[5.4.0]undec-7-ene |
| DCC | N,N'-dicyclohexylcarbodiimide |
| DCM | Dichloromethane |
| DIBAL | Di-iso-butylaluminum hydride |
| DMF | N,N-dimethylmethanamide |
| DMSO | Dimethyl sulfoxide |
| EDC · HCl | 1-Ethyl-3-(3-dimethylaminopropyl)carbodiimide hydrochloride |
| MTBE | 2-Methoxy-2-methylpropane |
| MW | Molecula weight |
| NMP | 1-Methyl-2-pyrrolidone |
| PPB | p-Phenyl-benzoyl |
| TEMPO | 2,2,6,6-Tetramethyl-piperidin-1-oxyl |
| THF | Tetrahydrofuran |
| THP | Tetrahydropyran |

The invention claimed is:

1. A process for preparing a prostaglandin or prostaglandin analog comprising:
reducing a compound of the formula (I)

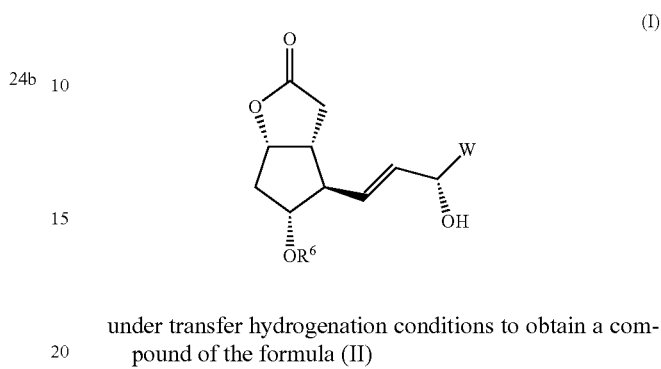

under transfer hydrogenation conditions to obtain a compound of the formula (II)

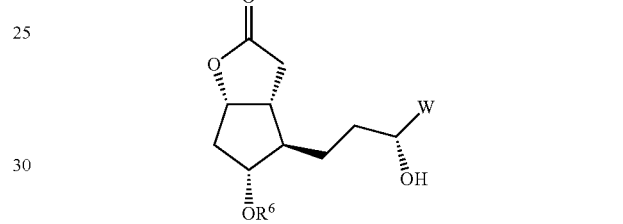

wherein
W represents a substituent selected from the group consisting of substituted and unsubstituted C$_1$-C$_6$ alkyl, C$_7$-C$_{16}$ aralkyl, wherein the aryl group is optionally substituted with one to three substituents selected from the group consisting of C$_1$-C$_6$ alkyl, halo and CF$_3$, and (CH$_2$)$_n$OR$^a$, wherein n is from 1 to 3 and R$^a$ represents a C$_6$-C$_{10}$ aryl group, which is optionally substituted with one to three substituents selected from the group consisting of C$_1$-C$_6$ alkyl, halo and CF$_3$;

and wherein

R$^6$ represents H or R$^2$ with R$^2$ comprising a hydroxyl protecting group;

and wherein the reduction of a compound of formula (I) under transfer hydrogenation conditions comprises contacting the compound with a hydrogen-donor selected from the group consisting of carboxylic acids and carboxylic acid derivatives, alcohols, dehydrogenatable hydrocarbons, and mixtures thereof, in the presence of a catalyst selected from the group consisting of Raney nickel and noble metal catalysts selected from the group consisting of rhodium, palladium, and platinum.

2. The process according to claim 1, wherein the prostaglandin or prostaglandin analog is a prostaglandin of general formula 16:

16

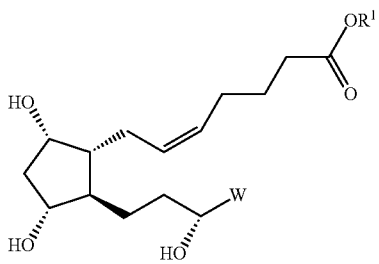

wherein $R^1$ is selected from the group consisting of $C_1$-$C_6$ alkyl; and

W represents a residue selected from the group consisting of substituted and unsubstituted $C_1$-$C_6$ alkyl, $C_7$-$C_{16}$ aralkyl wherein the aryl group is optionally substituted with one to three substituents selected from the group consisting of $C_1$-$C_6$ alkyl, halo and $CF_3$, and $(CH_2)_nOR^a$ wherein n is from 1 to 3 and $R^a$ represents a $C_6$-$C_{10}$ aryl group which is optionally substituted with one to three substituents selected from the group consisting of $C_1$-$C_6$ alkyl, halo and $CF_3$.

3. The process according to claim 1, wherein $R^6$ represents $R^2$ and the compound of formula (I) is obtained by a process comprising the steps (a) oxidizing a compound of general formula 17,

17

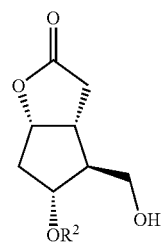

to obtain a compound of general formula 18,

18

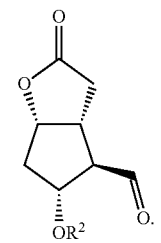

(b) Wittig reaction of the compound of formula 18 to obtain a compound of formula 20

20

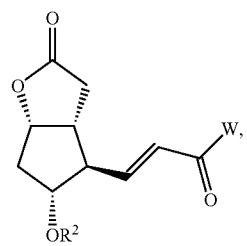

(c) reduction of the compound of formula 20 to obtain a compound of formula (VII)

21

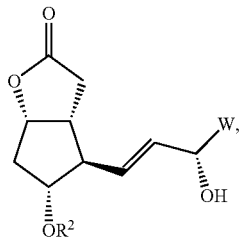

wherein W and $R^2$ are defined according to claim 1.

4. The process according to claim 1, wherein $R^6$ represents H and the compound of formula (I) is obtained by a process comprising the steps (a) oxidizing a compound of general formula 17

17

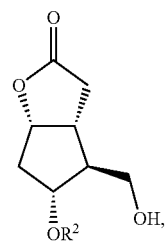

to obtain a compound of general formula 18,

18

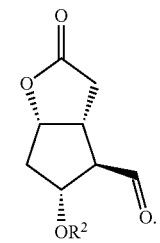

(b) Wittig reaction of the compound of formula 18 to obtain a compound of formula 20

20

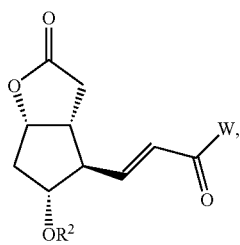

(c) reducing the compound of formula 20 to obtain a compound of formula 21

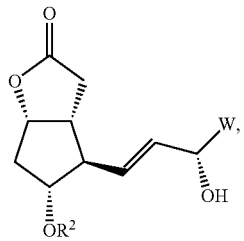

21

(d) deprotecting the compound of formula 21 to obtain a compound of formula 22

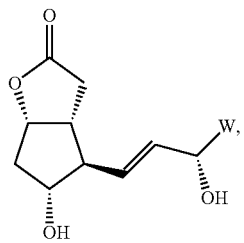

22 wherein W and R² are defined according to claim 1.

5. The process according to claim 1, wherein R⁶ represents R² and the process additionally comprises the steps of (w) deprotecting the compound of general formula (II) to obtain a compound of general formula 23

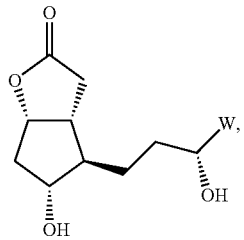

23

(x) reducing the compound of formula 23 to obtain a compound of formula 24

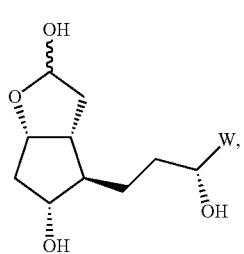

24

(y) Wittig reaction of the compound of formula 24 to obtain a compound of formula 25

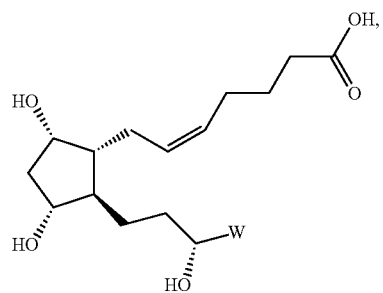

25

(z) deriving the compound of general formula 25, wherein W and R² are defined according to claim 1.

6. The process according to claim 1, wherein R⁶ represents H and the process additionally comprises the steps (x) reducing the compound of formula (II) to obtain a compound of formula 24

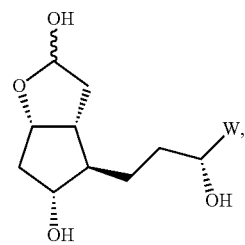

24

(y) Wittig reaction of the compound of formula 24 to obtain a compound of formula 25

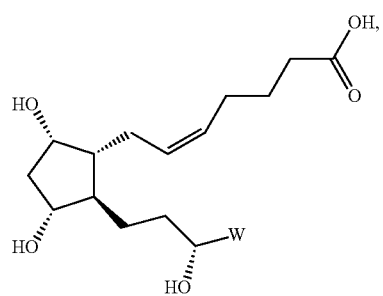

25

(z) deriving the compound of general formula 25, wherein W is defined according to claim 1.

7. The process according to claim 3, wherein the oxidation according to step (a) is carried out using DMSO or DMSO in combination with an activating agent selected from the group consisting of oxalyl chloride, SO₃.pyridine, DCC, EDC.HCl, and trifluoroacetic anhydride as an oxidizing agent.

8. The process according to claim 1, wherein the prostaglandin is latanoprost.

9. The process according to claim 1, wherein in the reduction of a compound of formula (I), a compound of general formula (III) is formed as a side product:

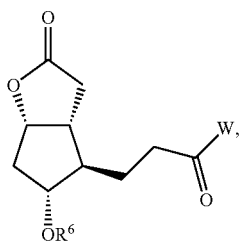

(III)

wherein R⁶ and W are defined according to claim 1,
and the compound of formula (III) is separated from the compound of general formula (II) by a process comprising the steps (1) reductive amination, and
(2) acidic extraction.

10. The process according to claim 9, wherein in step (1) a compound of general formula (IIIa) or (IIIb) is formed which is separated from the compound of general formula (II) according to step (2):

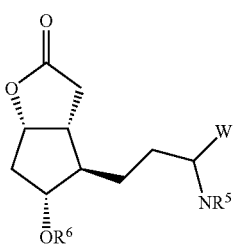

(IIIa)

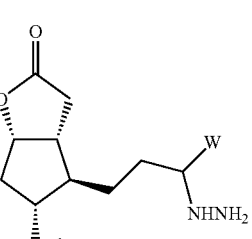

(IIIb)

wherein
W represents a residue selected from the group consisting of substituted and unsubstituted $C_1$-$C_6$ alkyl, $C_7$-$C_{16}$ aralkyl wherein the aryl group is optionally substituted with one to three substituents selected from the group consisting of $C_1$-$C_6$ alkyl, halo and $CF_3$, and $(CH_2)_n R^a$ wherein n is from 1 to 3 and $R^a$ represents a $C_6$-$C_{10}$ aryl group which is optionally substituted with one to three substituents selected from the group consisting of $C_1$-$C_6$ alkyl, halo and $CF_3$, $R^6$ represents hydrogen or $R^2$ with $R^2$ being a hydroxyl protecting group, and $R^5$ represents an alkyl, aryl, or aralkyl moiety.

11. The process according to claim 10, wherein in step (1), a compound of general formula 29, 30, 32 or 33 is formed:

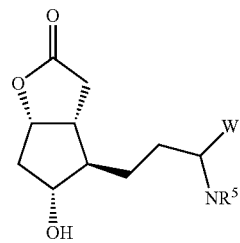

29

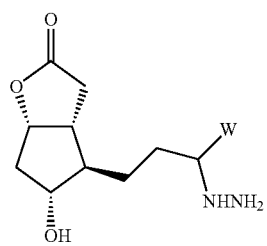

30

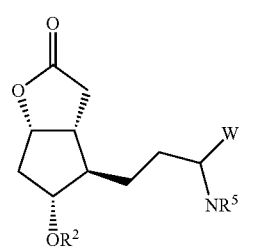

32

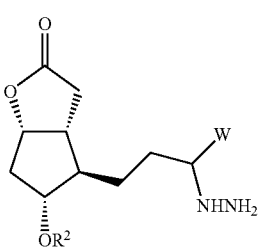

33 wherein W, $R^2$ and $R^5$ are defined according to claim 10.

12. The process according to claim 1, wherein the prostaglandin or prostaglandin analog is prepared by a process consisting of the steps of:

(a) oxidizing a compound of general formula 17,

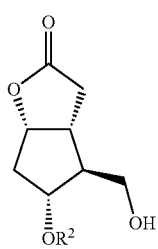

17 to obtain a compound of general formula 18,

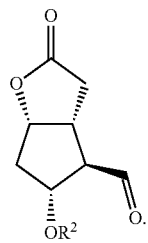

18

(b) Wittig reaction of the compound of formula 18 to obtain a compound of formula 20

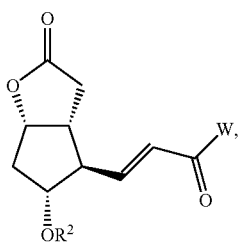

20

(c) reduction of the compound of formula 20 to obtain a compound of formula 21

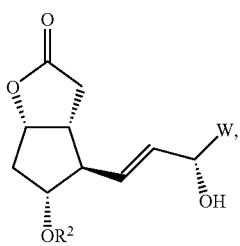

21

(d) deprotection of the compound of formula 21 to obtain a compound of formula 22

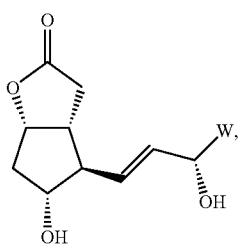

22

(i) reduction of a compound of general formula 22 under transfer hydrogenation conditions to obtain a compound of general formula 23

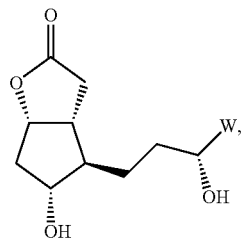

23

(x) reduction of the compound of formula 22 or 23 to obtain a compound of general formula 24

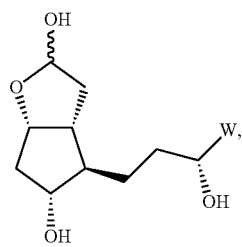

24

(y) Wittig reaction of the compound of general formula 24 to obtain a compound of formula 25

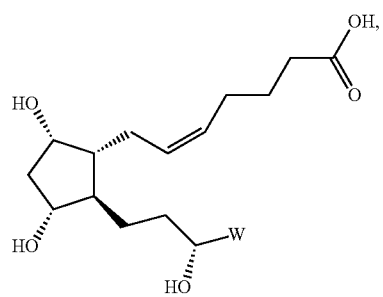

25

(z') derivatisation of the compound of general formula 25 to obtain a compound of general formula 16

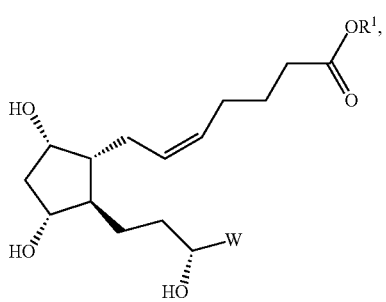

16 wherein
R$^1$ is selected from the group consisting of C$_1$-C$_6$ alkyl;
R$^2$ represents a hydroxyl protecting group; and
W represents a residue selected from the group consisting of substituted and unsubstituted C$_1$-C$_6$ alkyl, C$_7$-C$_{16}$ aralkyl wherein the aryl group is optionally substituted with one to three substituents selected from the group consisting of $C_1$-$C_6$ alkyl, halo and $CF_3$, and $(CH_2)_n OR^a$ wherein n is from 1 to 3 and $R^a$ represents a $C_6$-$C_{10}$ aryl group which is optionally substituted with one to three substituents selected from the group consisting of $C_1$-$C_6$ alkyl, halo and $CF_3$.

13. The process according to claim 12, wherein one or more of the intermediates of general formula 18 or 22 or 23 or 25 is obtained in solution and is used for the subsequent step without further purification.

* * * * *